United States Patent [19]

Nathanson

[11] Patent Number: 4,902,690
[45] Date of Patent: Feb. 20, 1990

[54] PEST CONTROLLING COMPOSITIONS

[75] Inventor: James A. Nathanson, Wellesley, Mass.

[73] Assignee: The General Hospital Corporation, Boston, Mass.

[21] Appl. No.: 218,491

[22] Filed: Jul. 6, 1988

Related U.S. Application Data

[63] Continuation of Ser. No. 605,845, May 1, 1984, abandoned.

[51] Int. Cl.$^4$ .................. A01N 43/90; A01N 43/50
[52] U.S. Cl. .............................. 514/213; 514/396; 424/DIG. 8; 424/DIG. 10
[58] Field of Search ............ 514/261, 263, 183, 396, 514/454, 453, 47; 424/DIG. 10, DIG. 8

[56] References Cited

U.S. PATENT DOCUMENTS

| | | | |
|---|---|---|---|
| 2,937,118 | 6/1956 | von Haxthausen et al. | 514/352 |
| 3,135,754 | 8/1962 | Hitchings et al. | 544/276 |
| 3,978,213 | 1/1975 | Lapinet et al. | 424/180 |

OTHER PUBLICATIONS

Hollingworth, R. M. & Mandock, L. L., Scientific Papers of the Institute of Organic ... #22, Conf. #7, 1980,
Hollingsworth et al., Science 208:74-76, 1980.
Evans, Nature, 287:60-62, 1980.
Nathanson et al., Mol. Pharm., 20:68-75, 1980.
Chang et al., J. Agricultural Food Chemistry, 25:493-501, 1977.
Seamon et al., J. Med. Chem., 26:432-439, 1983.
Nathanson et al., Science 180:308-310, 1973.
Nathanson et al., Science, 203:65-68, 1979.
Rojakovick et al., Post. Bioch. & Phys., 6:10-19, 1976.
Moffett et al., Comp. Biochem. Phys., 75C:305-310, 1983.
Bodnarqk, Chem. Abst., 98:29642U, 1983.
King, Chem. Evaluated on Insecticide and Repellents, 1954, pp. 1-21, 100, 101, 322 and 323.
Nathanson, J. A., in Trace Amines and the Brain, Usdin, E., and Sandler, M. (editors), pp. 161-190, (1976).

Primary Examiner—John W. Rollins
Attorney, Agent, or Firm—Saidman, Sterne, Kessler & Goldstein

[57] ABSTRACT

A pest-controlling composition which comprises:
(A) a first compound capable of substantially inhibiting a phosphodiesterase enzyme (PDE) of said pest; and
(B) a second compound having pest-dontrolling activity towards said pest, selected from the group consisting of
 (1) a substantial octopamine agonist toward an octopamine receptor present in said pest;
 (2) a compound directly and substantially stimulating the enzyme, adenylate cyclase; and
 (3) a cyclic adenosine monophosphate (cAMP) analogue.

16 Claims, 13 Drawing Sheets

8-∅-THEO = 8-PHENYLTHEOPHYLLINE

PEST CONTROLLING COMPOSITIONS

This application is a continuation of application Ser. No. 605,845, filed 5/1/84, abandoned.

BACKGROUND OF THE INVENTION

1. Field of the Invention

The present invention relates to pest controlling compositions formed by mixing a first compound having pest controlling activity together with a second compound capable of inhibiting a phosphodiesterase enzyme of the pest. The invention also relates to methods of controlling pests by treatment with the aforementioned compositions.

2. Description of the Background Art

Despite the recent development and great promise of such advanced pest controlling compositions as chemical sterilants, pheromones or ecologically-based insect control strategies, it is doubtless that, at present, the use of chemical pesticides still plays a predominant role. The use of insecticides often represents the difference between profitable crop production for farmers and no marketable crop at all, and the value of insecticides in controlling human and animal diseases has been dramatic.

Therefore, in parallel to the aforementioned newer technologies for pest control, there has been active research and investigation into the detailed biochemical modes of action of existing known chemical pesticides. Thus, for example, Nathanson et al., *Molecular Pharmacology* 20:68–75 (1981) presented evidence indicating that the formamidine pesticides chlordimeform (CDM) and N-demethylchlordimeform (DCDM) may affect octopaminergic neurotransmission. CDM and DCDM have been reported to mimic the effects of octopamine in stimulating light emission in the firefly lantern (Hollingworth, R. M. et al., *Science*, 208:74–76 (1980)), and in effecting nerve-evoked muscle responses in the locust leg (Evans, P.D., *Nature*, 287:60–62 (1980)). Nathanson et al., supra, found that DCDM, which is the probable in vivo metabolite of CDM, is about six-fold more potent than octopamine itself as a partial agonist of light organ octopamine-stimulated adenylate cyclase. Stimulation by the formamidines resulted in increased formation of the intracellular messenger, cyclic AMP. This stimulation was blocked by cyproheptadine, clozapine, fluphenazine and phentolamine compounds, also known to block the octopamine receptor. Nathanson et al. concluded that DCDM is the most potent octopaminergic compound described.

Similar results were observed by Hollingworth et al. (reported in the Scientific Papers of the Institute of Organic and Physical Chemistry of Wroclaw Technical University, No. 22, Conference 7 (1980)). These authors demonstrated that certain formamidines act on octopamine receptors to induce the synthesis of cyclic AMP, and that this response is blocked by both phentolamine and cyproheptadine, which are known to act as octopaminergic antagonists in insects. The authors also suggested that these formamidines are potent stimulators of the octopamine sensitive adenylate cyclases in the thoracic ganglia of *Periplaneta americana*, and in the ventral nerve cord and fat body of *M. sexta*. The authors suggest that the stimulation of octopamine receptors underlies a number of toxic responses seen with formamidines on insects.

It should be noted that the presence of an insect adenylate cyclase enzyme which is sensitive to octopamine as a "neuro transmitter" has been known for some time (Nathanson et al, *Science*, 180:308–310 (1973) (cockroach); Nathanson, ibid: 203: 65–68 (1979) (firefly); Evans, J., *Neurochem*, 30:1015–1022 (1978) (cockroach)).

The study of cyclic AMP (cAMP) as a "second messenger" has led to the accepted model that a hormone or neurotransmitter binds at a cell-membrane bound receptor, which activates adenylate cyclase to a form capable of converting ATP in the cytoplasm of the cell into cAMP. cAMP then relays the signal brought by the hormone or neurotransmitter from the membrane to the interior of the cell. Agonists of the hormone or neurotransmitter are, by definition, capable of eliciting the same response (see, for example, Nathanson and Greengard, *Scientific American*, 237:108–119 (1977)). Once formed inside the cell, cyclic AMP presumably binds to a protein kinase which is then capable of phosphorylating appropriate proteins, etc.

Given the continuous need for increased selectivity and effectiveness in pest control agents, it became desirable that the greater understanding of the biochemical mode of action of the formamidines be utilizable in some manner to improve their effectiveness, and to lead to a general rational formulation of pest control agents.

SUMMARY OF THE INVENTION

The present invention arose out of the initial observations by the inventor and others that the mode of action of certain formamidine pesticides was through their octopaminergic agonist activity on octopamine receptors present in the pest, and that these pest control agents were acting through generation of cAMP as a "second messenger." The inventor then observed that the effectiveness of any octopaminergic agonist pest control agent could be greatly enhanced when the quantity and half-life of generated cAMP was regulated by inhibiting insect phosphodiesterase enzymes, which are capable of hydrolyzing cAMP. Thus, addition of phosphodiesterase inhibitors to octopaminergic agonist pest control agents increases the action and effectiveness of these types of agents. Large amounts of experimental data have confirmed the generality of this invention.

Thus, in one embodiment, the present invention provides a pest controlling composition which comprises:
(A) a first compound capable of inhibiting a phosphodiesterase enzyme of said pest; and
(B) a second compound having pest-controlling activity towards said pest, selected from the group consisting of
 (1) an octopamine agonist toward an octopamine receptor present in said pest;
 (2) a compound directly stimulating the enzyme adenylate cyclase; and
 (3) a cyclic adenosine monophosphate (cAMP) analogue.

These compositions are synergistic, i.e., the combination of the first compound (A) and the second compound (B) results in the correlated action of both compounds which, together, have greater total effect than the sum of their individual effects.

The synergism observed in the compositions of the present invention should be distinguished from the more classical insecticide synergism. Thus, for example, it is known that pyrethrin insecticides, when used alone, have reversible action due to the detoxication effect by microsomal insect oxidases. Since the detoxication enzymes are inhibited by a number of compounds, especially those of the methylenedioxyphenyl structure, these compounds (called "synergists"), when used at various ratios, activate the pyrethrins by about 2 to 30 times. (See, for example, *Encyclopedia of Chemical Technology*, 3d Edition, Vol. 13, pages 424–425.)

Microsomal oxidase inhibitors inhibit enzymes which are directly involved in the destruction of insecticides. In the present invention, on the other hand, the phosphodiesterase inhibitors do not act on enzymes involved in the destruction of the octopamine agonist, but inhibit the hydrolysis of cyclic AMP acting as "secondary messenger."

FIG. 21 indicates the three types of pest control agents having pest control activity useful as compounds (B). These are either octopamine agonists (B1), direct adenylate cyclase enzyme stimulators (B2), or cyclic AMP analogues (B3). Octopamine agonists act by binding to a receptor which activates adenylate cyclase which, in turn, produces secondary messenger cyclic AMP. Enzyme stimulators also act through the production of cyclic AMP, but do so by interacting directly with adenylate cyclase, bypassing the receptor. Once octopamine agonists or enzyme stimulators lead to the production of cyclic AMP, the cyclic AMP can either be hydrolyzed by the action of phosphodiesterase enzymes (PDE) or bind to a cyclic AMP receptor generating hormonal-type activity. The third type of pest control compound, the cyclic AMP analogue (B3), can either be hydrolyzed by the action of PDE or bind to a cyclic AMP receptor generating hormonal-like activity.

With all three types of pest control agents, the addition of PDE inhibitors blocks or decreases the competing hydrolyses of the cyclic AMP or cyclic AMP analogue, increasing hormonal-like and pest control activity.

In another embodiment of the invention, there is provided a method for controlling pests by treating said pests with a composition as hereinabove in an amount effective to provide pest control, by either pesticidal or pestistatic activity.

DESCRIPTION OF THE PREFERRED EMBODIMENTS

Figure 1:
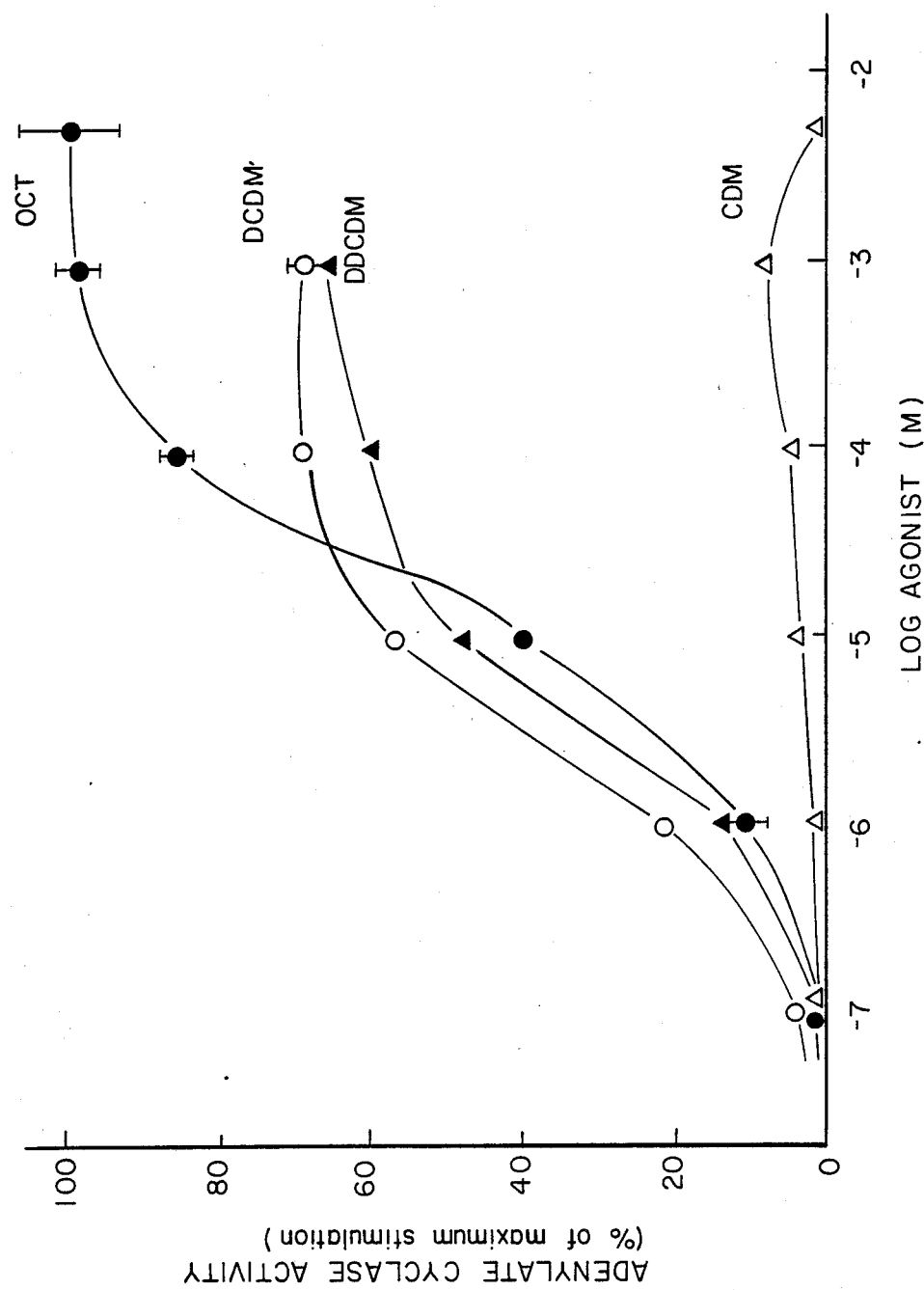
FIG. 1 shows the agonist activity of three formamidine compounds using the firefly lantern octopamine receptor. DCDM: mono-demethylchlorodimeform; DDCDM: di-demethylchlorodimeform; OCT: octopamine; CDM: chlorodemeform.

The terms "pest controlling" or "pest controlling activity," used throughout the specification and claims, are meant to include any pesticidal (killing) or pestistatic (preventing the host plant from being eaten, or inhibiting, maiming or generally interfering) activities of a composition against a given pest at any stage in its life cycle. Thus, these terms not only include killing, but also include such activities as the production of behavioral abnormalities (e.g., tremor, incoordination, hyperactivity, anorexia, leaf walk-off behavior) which interfere with such activities such as but not limited to eating, molting, hatching, mobility or plant attachment. The terms also include activities of chemisterilants which produce sterility in insects by preventing the production of ova or sperm, by causing death of sperm or ova, or by producing severe injury to the genetic material of sperm or ova, so that the larvae that are produced do not develop into mature progeny.

The terms also include repellants, which are substances that protect animals, plants or products from insect attack by making food or living conditions unattractive or offensive. These may be poisonous, mildly toxic, or non-poisonous.

The terms also include attractants, food lures, sex pheromones, aggregation pheromones, and the like. Any compound (B) which has such "pest controlling activity" as defined and which is (i) an octopamine agonist toward an octopamine receptor present in the pest, (ii) a direct stimulator of pest adenylate cyclase, or (iii) a cyclic AMP analogue, is included in the present invention.

The question of whether a given compound (B) is an octopamine agonist (B1) can be readily answered by measuring adenylate cyclase activity of the octopamine-sensitive adenylate cyclase present in broken cell preparations of the firefly light organ. Generally, the broken cell preparations are prepared according to the method described in a paper by Nathanson et al. (*Molecular Pharmacology* 20:68–75 (1981), which is herein incorporated by reference. Specimens of *Photinus pyralis* are prepared by opening their tail sections, cleaning them, removing the light organs, and homogenizing the cyclase-containing fraction. Adenylate cyclase activity is measured in appropriate buffer-containing ATP and the compound to be tested. If necessary, the compounds (B) to be tested are initially solubilized and appropriate solvent controls are run in parallel. The enzyme reaction is initiated by addition of ATP, stopped by heating, and centrifuged. Cyclic AMP can be measured by any test which indicates the presence thereof, preferably by the protein binding assay of Brown et al. (*Advances in Cyclic Nucleotide Research* 2:25–40 (1972)). Normally, the solution mixture contains a phosphodiesterase inhibitor such as theophylline, so as to provide linear measurements with respect to time and enzyme concentration. The determination of the constant $K_a$, which is the concentration of agonist B1 necessary for halfmaximal activation of cyclase activity, is carried out by measuring cyclase activity in the preparation, and plotting the activity (above control activity) versus the semilogarithm of the particular agonist concentration. This is done for a series of increasing concentrations until maximal activity (Vmax) is reached. $K_a^B$ is then calculated from the graph as the agonist concentration required for one-half of Vmax. $K_a^B$ is compared with the constant ($K_a^{oct}$) determined in an analogous way using ± p-octopamine as the agonist. The ratio $K_a^{oct}/K_a^B$ is then an indication of whether the compound (B1) is better (ratio greater than 1) or worse (ratio smaller than 1) than (±)-p-octopamine. Maximal activation of enzyme activity as a percentage of maximal activation seen in the presence of (±) p-octopamine can be denoted as % Vmax.

Generally, an octopamine agonist having a $K_a^{oct}/K_a^B$ ratio greater than 0.05, preferably 0.05 to 1000, most preferably 0.1 to 1000, as measured by the firefly lantern test, is used. Also, generally, octopamine agonists having Vmax anywhere between 5 and upwards of 100%, preferably between 10 and upwards of 100%, of the Vmax of (±)-p-octopamine can be used. The values of Vmax for any desired octopamine agonist are not as important as the values of the ratio of K's. As long as the $K_a^{oct}/K_a^B$ ratio falls within the stated range, the Vmax values can vary widely.

In addition to the above method employing the firefly light organ, octopamine-sensitive adenylate cyclase can also be measured in tissue preparations from the nerve cord of any desired particular insect pest, using a modification of the method appearing in Nathanson et al. (*Science* 180:308–310 (1973)) herein incorporated by reference. In this modification (which is not necessary if the firefly light organ is used), dopamine (10 micromolar) and serotonin (10 micromolar) are added to all (including control) assay tubes. This is done in order to be sure that the tested compounds (B1) are affecting only octopamine receptors (known to be present in all insect nerve cords) and not dopamine or serotonin receptors. Otherwise, the procedure is identical to that described above.

Among the preferred octopamine agonists B1 are those belonging to the families of the phenylethylamines (I):

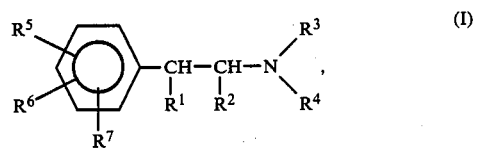

Cyclic Amidines (II):

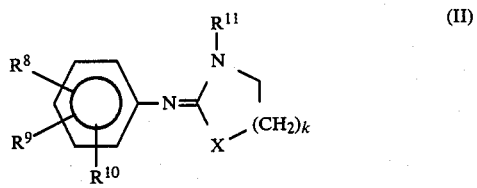

where X is N—$R^{11}$, O, $CH_2$, or S, and n may be 1 or 2; such as 2-(phenylimino) imidazolidines (X=NH, n=1); 2-(phenylimino) pyrrolidines (X=$CH_2$, n=1); 2-(phenylimino) oxazolidines (X=O, n=1); 2-(phenylimino) thiazolidines (X=S, n=1) and 2-(phenylimino) thiazines (X=S, n=2). See, e.g., the compounds in DeJong et al, Europ. J. Pharm. 69:175–188 (1981);

2-benzylimidazolines (III):

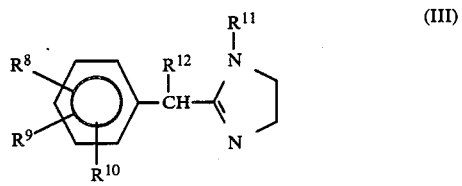

Formamidines (IV):

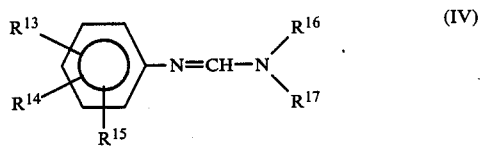

$R^3$, $R^4$, $R^{11}$, $R^{16}$ and $R^{17}$ stand for hydrogen, lower alkyl or lower alkyl substituted by hydroxy or lower ($C_1$–$C_6$) alkoxy; $R^{12}$ stands for hyrogen or hydroxyl. $R^1$ and $R^2$ are the same or different and selected from the group consisting of hydrogen, hydroxy and lower ($C_1$–$C_6$) alkyl; $R^5$, $R^6$, $R^7$, $R^8$, $R^9$, $R^{10}$, $R^{13}$, $R^{14}$, and $R^{15}$ are the same or different and selected from the group consisting of hydrogen, hydroxy, fluorine, chlorine, bromine, iodine, nitro, lower ($C_1$-$C_6$) alkyl, lower ($C_1$-$C_6$) alkoxy, lower haloalkyl, amino, mono lower alkylamino, di-lower alkyl amino, hydroxy-substituted lower alkyl and lower acylamino.

Also, in compounds of formulae (II) or (III) above $R^8$, $R^9$ or $R^8$, $R^{10}$ together may form a six membered phenyl, pyridine, diazine, or cyclohexyl ring fused to the noted phenyl ring. For example, systems of formulae V and VI can also be used:

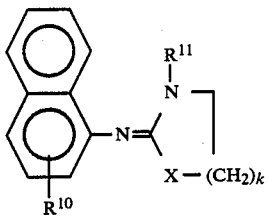
(V)

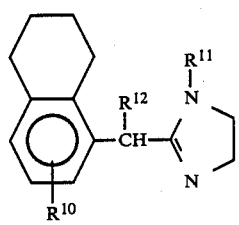
(VI)

where $R^{10}$, $R^{11}$, $R^{12}$ and n are as defined previously.

Specific compounds useful as octopamine agonists (B1) include phenylethylamines of the formula (VII):

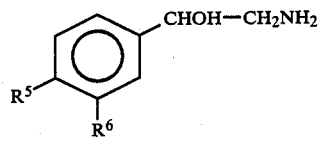
(VII)

where $R^5$ is OH and $R^6$ is $CH_3$, $C_2H_5$, i-$C_3H_7$, $C_6H_{11}$, $NH_3$, F, Cl, Br I, $NHSO_2CH_3$, OH, H or $OCH_3$; or where $R^6$ is OH and $R^5$ i-$C_3H_7$, $CH_3$, $C_2H_5$, $C_6H_{11}$, $NH_3$, Cl, Br, I, $NH SO_2CH_3$, $OCH_3$ or H.

Other specific compounds B1 include cyclic amidines of the formula (VIII):

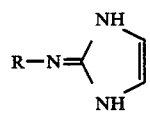
(VIII)

where R is phenyl; o-tolyl; 2,6 dimethylphenyl; 2,3 (cyclohexyl) phenyl; 2,6-diethylphenyl; 2,6-difluorophenyl; 2-chlorophenyl; 2,6-dichlorophenyl; 3-chlorophenyl; 2,5-dichlorophenyl; 3,5-dichlorophenyl; 5-bromoquinoxaline; 2-methyl,3-bromophenyl; 2-chloro,3-methylphenyl, 2-chloro,4-methylphenyl; 3-fluoro,6-methyl-phenyl; 2,6-dichloro, 4-hydroxyphenyl; 3,4-dihydroxyphenyl; or 4-chlorophenyl.

Other specific compounds B1 include cyclic amidines of the formula (IX):

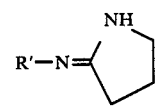
(IX)

where R' is phenyl, o-tolyl, 2,6-dimethylphenyl, 2-chlorophenyl, 2,6-dichlorophenyl, 4-chlorophenyl, or 4-methoxyphenyl.

Other specific compounds B1 include cyclid amidines of the formula (X):

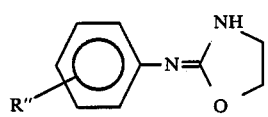
(X)

where R" is H, 2-$CH_3$, 2-6-di$CH_3$, 4-$CH_3$, 4-Cl or 2,6-diCl. Other specific compounds B1 include cyclic amidines of the formula (XI):

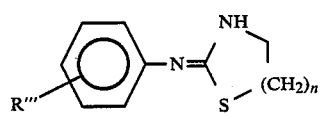
(XI)

where R'" is 2,6-dimethyl; 2,6-diethyl; 2,6-dichloro; 2,4,6-trimethyl; 2,4-dichloro; 2,4-dimethyl; 2-chloro-4-methyl; 4-chloro-2-methyl; 4-chloro; 2-chloro; 2-methyl or 4-methyl; where n is 1 or 2.

Other specific compounds B1 include 2-benzylimidazoline of the formula (XII):

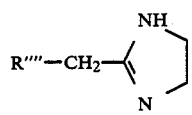
(XII)

where R"" is phenyl, o-tolyl, 2,6-dichlorophenyl, 4-$CH_3O$ phenyl, 2,3 naphthyl (naphazoline), 2,6-dimethyl, 4-$^t$Butylphenyl (xylometazoline), 2,6-dimethyl, 3-hydroxy, 4-$^t$Butylphenyl (oxymetazoline), or

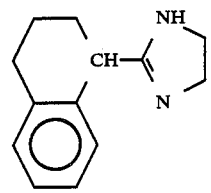

(tetrahydrozoline).

The syntheses and preparation of phenylethylamines of formula (I) is described, for example, in LeClerc et al., J. Med. Chem. 23:738–744 (1980). The syntheses and preparation of cyclic amidines of formulas (II) or (III) is described, for example, in Rouot, et al., Journal of Medicinal Chemistry, Vol. 19, 1049 (1976); Oxley et al, J. Chem Soc., 497 (1947), Faust et al., J. Org. Chem. 26:4044 (1961); Van der Stelt et al., Arzneim. Forsch 15:1251 (1965) or Jen et al., J. Med. Chem 15:727 (1972) and ibid, 18:90 (1975). The syntheses and preparation of formamidines of formula (IV) can be found, for example, in Chang et al, J. Agric. Food Chem. 25:493–501 (1977).

Also, it should be noted that applicant has filed on even date a commonly assigned patent application entitled "Pest Controlling Agents" having Ser. No. 605,847, now U.S. Pat. No. 4,678,775 which discloses a number of formamidine, cyclic amidine and phenylethylamine octopamine agonists as pest-controlling agents. The full disclosure of this copending patent application is herein incorporated by reference.

Other examples of specific compounds (B1) which are octopamine agonists are listed in the Tables in accompanying examples.

The second type of pest controlling compounds (B2) useable in the present compositions are direct stimulators of the pest enzyme adenylate cyclase. These compounds bypass the receptor, and interact with one or another of the associated catalytic or regulatory subunits of adenylate cyclase, thereby stimulating the formation of cyclic AMP. Suitable compounds can be determined from assay of pest adenylate cyclase as described above. Generally, a compound (at a concentration of less than 1 millimolar) causing a stimulation of adenylate cyclase of at least 10% that due to a Vmax concentration of (±)-p-octopamine is preferred. A direct stimulator of adenylate cyclase can be distinguished from an octopamine agonist in that the stimulatory activity of the former (but not the latter) at a concentration causing half-maximal activation of the enzyme, is not significantly reduced by the addition of known octopamine receptor antagonists, such as phentolamine or cyproheptadine, used at a concentration of 100 micromolar.

Among preferred direct enzyme stimulators are those belonging to the diterpenes, (XIII), forskolin (XIV) and its derivatives:

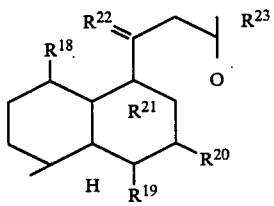

$R^{18-23}$ stand for hydrogen, hydroxyl, oxy, keto, lower alkyl, lower alkene, lower alkoxy, carboxy and carboxyamino.

In forskolin $R^{18}=R^{19}=R^{21}=OH$; $R^{20}=OCOMe$; $R^{22}=O$; and $R^{23}=CH=CH_2$.

Certain bacterial-derived toxins, such as cholera toxin can also be used.

The preparation of forskolin derivatives is described in Seamon, K. and Daly, J. W, *J. Med. Chem.* 26:436-439 (1983). The structure and action of cholera toxin are described in Van Heyningen, S., *Biosci. Repts.* 2:135-146 (1982).

The third type of pest controlling compounds (B3) useable in the present compositions are cyclic adenosine monophosphate analogues. These are compounds which havecyclic AMP activity, and are capable of binding to the appropriate pest protein kinase to activate the same. The potency of a particular cyclic AMP analogue can be determined from the calculated $K_a$ and Vmax of the analogue for activating cyclic AMP-dependent protein kinase found in insect nerve cord or firefly lantern, using the method described by Nathanson in *Cyclic AMP: A Possible Role in Insect Nervous System Function*, Ph.D. Thesis, Yale Univ., 1973, pp. 81-82, herein incorporated by reference. The $K_a$ and Vmax for the analogue can be compared, in the same tissue, with the $K_a$ and Vmax for cyclic AMP, itself, in stimulating protein kinase.

Generally, a cyclic AMP analogue with a $K_a^B/K_a$-(cyclic AMP) ratio greater than 0.01, preferably about 0.01 to 100 or more, most preferably 0.05 to 100 or more is used. Also, generally, cyclic AMP analogues having a Vmax anywhere between 5 and upwards of 100% of the Vmax for cyclic AMP can be used.

A number of biologically active cyclic AMP analogues have been synthesized. See Revankar and Robins, in *Handbook of Experimental Pharmacology*, 58/I (ed. J. Nathanson, J. Kebabian) pp. 17-151 (Spring-Verlag, N.Y.) 1982. Among the preferred ones are 6-n-butylamino-8-benzylthio-cyclic AMP; 8-p-chlorophenylthio-cyclic AMP; 8-chloro-cyclic AMP; 8-bromo-cyclic AMP; $N^6$-monobutyryl or $N^6,2'$-0-dibutyryl cyclic AMP; 7-deaza-cyclic AMP; and 1-deaza-cyclic AMP.

The compound (A) is one capable of inhibiting a phosphodiesterase enzyme of the pest being controlled. The inhibition is such that it should prevent or greatly decrease the hydrolysis of endogenous cAMP produced by activation of adenylate cyclase. Alternatively, the phospodiesterase inhibitor should be capable of inhibiting the hydrolysis of the cyclic adenosine monophosphate analogue. The inhibition of phosphodiesterase may be either through a competitive or non-competitive mode. Further, the phosphodiesterase should be that of the particular pest being controlled, but may generally also be the phosphodiesterase present in the broken cell preparations described previously, obtained from the firefly lantern. Thus, the testing of any particular PDE inhibitor can be carried out on isolated pest PDE's or specifically on firefly lantern PDE.

The ability of any compound (A) to inhibit phosphodiesterase (PDE) activity in broken cell preparations of firefly lantern or in pest tissues can be determined either (1) by measuring the decrease in rate of hydrolysis of an added amount of cyclic AMP by PDE (see Methods Section of Nathanson et al., *Mol. Pharmacol.* 12:390-398 (1975)), or (2) by measuring the rate of accumulation of one of the breakdown products of cyclic AMP, such as 5'-AMP or adenosine (see method of Filburn et al., *Anal. Biochem.* 52:505-516 (1973)). Both of these are herein incorporated by reference.

Generally, any compound capable of maximally inhibiting PDE activity by at least 50% ($V_{max}$-inhibition) and preferably by at least 80% is preferred. Also, in terms of the concentration of the compound required for such inhibition, this can be quantitated by determining the IC $_{50\text{-}inhibition}$, i.e., the concentration of the compound required to cause 50% of the maximal inhibition-caused by the compound at any concentration. Generally, any compound with an IC $_{50\text{-}inhibition}$ for PDE of less than 10 mM and preferably less than 2.5 mM is preferred.

Of particular interest are purine derivatives, such as caffeine, theophylline, xanthine, methylxanthine, isobutylmethylxanthine (IBMX), and lower alkyl or substitution homologues or analogues thereof. See, e.g. Kramer, et al., *Biochem*, 16:3316 (1977); Garst et al., *J. Med. Chem.*, 19:499 (1976); Amer et al., *J. Pharm. Sci.*, 64:1 (1975); or Beavo et al., *Mol. Pharm.*, 6:597 (1970). For the purposes of this invention, halide, hydroxy, keto, lower alkoxy, lower straight alkyl, lower branched alkyl, amino, lower alkylamino, lower halo alkyl, fluorine, chlorine, bromine, iodo, nitro, mercapto, alkeneoxy, cyano, alkyl-cyano, phenyl, benzyl, substituted benzyl, or the like substituents on any of the aforementioned compounds are equivalent if they do not interfere with the inhibitory activity of the PDE inhibitor, and do not substantially block the agonistic activity of the octopaminergic agonist.

Of interest are also the phosphodiesterase inhibitors described by Rojakovick et al., (*Pesticide Biochemistry and Physiology* 610-19 (1976)) which belong to the family of quinoxaline dithiols. These compounds, denoted as oxythioquinox, SAS 2185, 1948, 2501, 2061, 2551 or 2079, are those of the formula (XV):

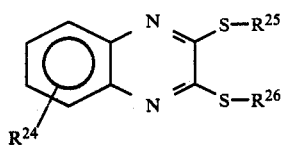

where $R^{24}$ can be hydrogen, lower alkyl, lower alkoxy or trifluoromethyl, $R^{25}$ and $R^{26}$ can be the same or different and selected from the group of H, $COOR^{27}$, where $R^{27}$ is lower alkyl; or both $R^{25}$ and $R^{26}$ taken together may form a group of the formula —CO—, bridging both S atoms. It should be noted that Rojakovick et al., found these compounds to be phosphodiesterase inhibitors, as determined by cockroach brain adenylate cyclase and PDE in vitro. However, the authors concluded that there was no direct relationship of the PDE inhibition activity to their mode of toxic action since, on the basis of broad distribution of PDE in the animal kingdom, it appeared unlikely to them that PDE inhibition was a direct cause of their selective pest controlling activity.

Another family of PDE inhibitors are the benzylisoquinoline derivatives, such as papaverine (See, for example, U.S. Pat. No. 3,978,213 to Lapinet et al., which relates to the cosmetic use of mixtures of cyclic AMP and phosphodiesterase inhibitors; or Amer et al., supra, p.17).

Another family of PDE inhibitors are the substituted pyrrolidones, such as 4-(3-cyclopentyloxy-4-methylphenyl)-2-pyrrolidine (ZK 62711). See Schwabe et al., *Mol. Pharmacol.* 12:900–910, 1976.

Another family of PDE inhibitors are the 4-(3,4-dialkoxybenzyl)-2-imidazolidinones, such as (4-(3-butoxy-4-methoxbenzyl)-2-imidazolidinone (Ro 20-1724). See Sheppard et al., *Biochem. J.* 120:20P (1970).

Another family of PDE inhibitors are the benzodiazepine derivatives, such as diazepam. See Dalton et al., *Proc. Soc. Exp. Bio. Med.* 145:407-10 (1974).

Another family of PDE inhibitors are the tricyclic agents, such as the phenothiazines. See Honda et al., *Biochim. Biophys. Acta* 161:267 (1968).

Another family are various purine-ribose derivatives, including puromycin and derivatives of cyclic nucleotides (other than cyclic AMP or active cyclic AMP analogues). See Amer et al., *J. Pharm. Sci.* 64:1-37 (1975) Table VI.

Anther PDE inhibitor is SQ20009:(1-ethyl-4-isopropylidenehydrazino-14-pyrazolo(3,4)pyridine-5-carboxylate ethyl ester. See Beer et al., *Science* 176:428 (1972).

In general, any compound which inhibits PDE as described above and which, at the same concentration, does not substantially block the activity of the octopaminergic agonist in stimulating octopamine-sensitive adenylate cyclase (as measured above), can be used.

The PDE inhibitor may be present alone or in combination with other active or non-active compounds. For example, it is known that tea leaves and coffee beans contain caffeine. Kaplan et al., *S.A. Med. T.* 48:510 (1974). Kola nuts also contain caffeine (*J. Food Sci.,* 38:911 (1973). Thus ground tea leaves, or kola nuts, when combined with any of the compounds (B) are covered by the present invention.

The molecular inhibition of PDE in vitro by a PDE inhibitor correlates with the molecular inhibition of the enzyme in vivo. However, it may be that a compound which is an excellent PDE inhibitor in vitro does not show good in vivo synergistic activity. Other factors, such as possible metabolism, transport or absorption of the compound may influence its overall effectiveness. One of skill in the art, however, can by a simple preliminary trial on the desired pest ascertain quite quickly and routinely whether a chosen agent is useful in vivo.

The % ratio by weight of compound (A) to compound (B) (octopamine agonist, direct enzyme stimulator, or cyclic adenosine monophosphate analogue), can be varied from 0.001% to 99.99%, preferably 10% to 90%. Preferably, the ratio is adjusted so as to effect maximal pesticidal or pestistatic effect in the combination.

The pest controlling compositions of the present invention can be formulated as dusts, water dispersions, emulsions, and solutions. They may comprise accessory agents such as dust carriers, solvents, emulsifiers, wetting and dispersing agents, stickers, deodorants and masking agents (see for example, *Encyclopedia of Chemical Technology*, Vol. 13, page 416 et seq.).

Dusts generally will contain low concentration, 0.1-20%, of the compound (B), although ground preparations may be used and diluted. Carriers commonly include organic flours, sulfur, silicon oxides, lime, gypsum, talc, pyrophyllite, bentonites, kaolins, attapulgite, and volcanic ash. Selection of the carrier can be made on the basis of compatibility with the desired pest control composition (including pH, moisture content, and stability), particle size, abrasiveness, absorbability, density, wettability, and cost. The mixture of the composition of the invention and diluent is made by a variety of simple operations such as milling, solvent impregnations, fusing and grinding. Particle sizes usually range from 0.5-4.0 microns in diameter.

Wettable powders can be prepared by blending the mixture of the invention in high concentrations, usually from 15-95%, with a dust carrier such as bentonite which wets and suspends properly in water. 1 to 2% of a surface-active agent is usually added to improve the wetting and suspendibility of the powder.

The pest-controlling composition can also be used in granules, which are pelleted mixtures of the composition, usually at 2.5-10%, and a dust carrier, e.g., adsorptive clay, bentonite or diatomaceous earth, and commonly within particle sizes of 250 to 590 microns. Granules can be prepared by impregnations of the carrier with a solution or slurry of the composition and can be used principally for mosquito larvae treatment or soil applications.

The composition can also be applied in the form of an emulsion, which comprises a solution of the composition in water immiscible organic solvents, commonly at 15-50%, with a few percent of surface active agent to promote emulsification, wetting, and spreading. The choice of solvent is predicated upon solubility, safety to plants and animals, volatility, flammability, compatibility, odor and cost. The most commonly used solvents are kerosene, xylenes, and related petroleum factions, methylisobutylketone and amyl acetate. Water emulsion sprays from such emulsive concentrates can be used for plant protection and for household insect control.

The composition can also be mixed with baits, usually comprising 1–5% of composition with a carrier especially attractive to insects. Carriers include sugar for house flies, protein hydrolysate for fruit flies, bran for grasshoppers, and honey, chocolate or peanut butter for ants.

The composition can be included in slow release formulations which incorporate non-persistent compounds, insect growth regulators and sex pheromones in a variety of granular microencapsulated and hollow fiber preparations.

The pest controlling compositions of the present invention will be applied depending on the properties of the particular pest controlling compound, the habits of the pest to be controlled and the site of the application to be made. It can be applied by spraying, dusting or fumigation.

Doses of the combined weight of the two active ingredients may typically vary between 0.001–100 lbs/acre, preferably between 0.001–5 lbs/acre.

Sprays are the most common means of application and generally will involve the use of water as the principal carrier, although volatile oils can also be used. The pest-control compositions of the invention can be used in dilute sprays (e.g., 0.001–10%) or in concentrate sprays in which the composition is contained at 10–98%, and the amount of carrier to be applied is quite reduced. The use of concentrate and ultra low volume sprays will allow the use of atomizing nozzles producing droplets of 30 to 80 microns in diameter. Spraying can be carried out by airplane or helicopter.

Aerosols can also be used to apply the pest controlling compositions. These are particularly preferred as space sprays for application to enclosures, particularly against flying insects. Aerosols are applied by liquified gas dispersion or bomb but can be generated on a larger scale by rotary atomizers or twin fluid atomizers.

A simple means of pest control composition dispersal is by dusting. The pest controlling composition is applied by introducing a finely divided carrier with particles typically of 0.5–3 microns in diameter into a moving air stream.

Any octopamine-receptor containing pest is treatable by the formulation of the present invention. These pests include all invertebrate pests, including, but not limited to, round worms (e.g., hookworm, trichina, ascaris); flatworms (e.g., liver flukes and tapeworms); jointed worms (e.g., leeches); molluscs (e.g., parasitic snails); and arthropods (insects, spiders, centipedes, millipedes, crustaceans (e.g., barnacles)). In particular, included among the arthropods are ticks; mites (both plant and animal); lepidoptera (butterflies and moths and their larvae); hemiptera (bugs); homoptera (aphids, scales); and coleoptera (beetles). Also included are spiders; anoplura (lice); diptera (flies and mosquitoes); trichoptera; orthoptera (e.g., roaches); odonta; thysanura (e.g., silverfish); collembola (e.g., fleas); dermaptera (earwigs); isoptera (termites); ephemerids (mayflies); plecoptera; mallophaga (biting lice); thysanoptera; siphonaptera (fleas); dictyoptera (roaches); psocoptera (e.g., book lice); and certain hymenoptera (e.g., those whose larva feed on leaves).

EXAMPLES

Having now generally described this invention, the same will become better understood by reference to certain specific examples which are included herein for purposes of illustration only and are not intended to be limiting unless otherwise specified.

IN VITRO METHODS

I. Determination of Octopamine Agonist Activity

A. Firefly Light Organ

Specimens of *Photinus pyralis* were collected in summer, frozen on dry ice, and stored at $-90°$. Under these conditions, octopamine sensitive enzyme activity remains stable for six months or longer. For each experiment, a number of insects were thawed and maintained at 4° C. Tail sections were opened through a dorsal midline incision and the abdominal cavity was cleaned out of all gut, fat reproductive organs, and ganglia. The light organs were then removed from the ventral cuticle, cleaned of any adhering nonlantern tissue, and homogenized (10 mg/ml) in 6 mM Tris-maleate buffer (pH 7.4). To prepare a $P_2$ fraction, the homogenate was diluted to a volume of 30 ml in 6 mM Tris-maleate and centrifuged at $120,000 \times g$ for 20 minutes. The supernatant was discarded, and the pellet was resuspended by homogenization in 30 ml of buffer and again centrifuged at $120,000 \times g$ for 20 minutes. The resulting pellet ($P_2$ fraction) was resuspended in a volume of 6 mM Tris-maleate equivalent to the starting amount and maintained at 0° until it was used. Alternatively, the homogenate may be used directly without preparing $P_2$ fraction.

Adenylate cyclase activation by test compounds was measured in test tubes containing (in 0.3 ml) 80 mM Tris-maleate, pH 7.4; 10 mM theophylline; 8 mM $MgCl_2$; 0.1 mM GTP; 0.5 mM ethylene glycol bis (beta-aminoethyl ether)-N,N,N'N'-tetraacetic acid; 2 mM ATP; 0.06 ml of $P_2$ fraction; and the various compounds to be tested. Prior experiments had determined that, under these conditions, octopamine-sensitive adenylate cyclase activity is optimized. Test compounds were initially solubilized (prior to aqueous dilution) in water or (if soluble) in 50% (v/v) methanol. If insoluble in 50% methanol, compounds may be dissolved initially in 100% methanol, or 100% dimethylsulfoxide, or 100% polyethylene glycol. Final solvent concentration after dilution can be kept as high as 15% for methanol and DSMO and as high as 20% for polyethylene glycol. Appropriate solvent controls were run in parallel. The enzyme reaction (5 minutes at 30°) was initiated by addition of ATP, stopped by heating to 90° for 2 minutes, and then centrifuged at $1000 \times g$ for 15 minutes to remove insoluble material. Cyclic AMP in the supernatant was measured by protein-binding assay, according to the method of Brown et al., *Adv. Cyclic Nucleotide Res.* 2:25–40 (1970). Under the above assay conditions, enzyme activity is linear with respect to time and enzyme concentration, and phosphodiesterase activity is nearly completely inhibited. Previous experiments had shown that the cyclic AMP produced in this reaction cochromatographs on Dowex AG-50X ® with authentic cyclic AMP. Protein concentration was determined by the method of Lowry et al., *Journal of Biological Chemistry* 193:265–275 (1951).

B. Other Pest Tissues

In those cases in which other pest tissues are used to measure octopamine agonist activity, the procedure is identical to that above, except that the tissue to be used is the brain, segmental ganglia, or the entire nerve cord of the insect pest, with or without the brain. The tissue is homogenized (usually 15 mg/ml) as above in 6 mM Tris maleate, pH 7.4. Assay conditions are identical to those described above except that dopamine (10 micromolar) and serotonin (10 micromolar) are added to all (including control) assay tubes when testing compounds which may affect receptors other than octopamine receptors. This is done to cancel out the effects of dopamine and serotonin receptors which are usually present in nerve cord. It assures that the compound (B) tested is affecting only octopamine receptors (known to be present in all insect nerve cords).

II. Determination of Adenylate Cyclase Stimulating Activity

As detailed previously, the adenylate cyclase assay, either in the firefly or in other insect pest, is also used to identify a direct stimulator of adenylate cyclase.

III. Determination of Cyclic AMP-Dependent Protein Kinase Activity (for Determination of Activity of Cyclic AMP Analolgues A $P_2$ pellet is prepared as described above from either firefly lantern or insect pest nerve tissue. In this assay, the pellet is used both as a source of protein kinase and as the substrate which is phosphorylated. The assay mixture (total volume 0.2 ml) contains: 10 micromoles sodium glycerol phosphate buffer, pH 7.4; 1 millimicromole gamma-$^{32}$P-ATP, approx. $10^6$ cpm; 2 micromoles $MgCl_2$; 2 micromoles NaF; 0.4 micromoles theophylline; 0.06 micromoles EGTA; 10–100 micrograms protein of $P_2$ pellet; ± various concentrations of cyclic AMP or the cyclic AMP analogue to be tested (typically to give a final concentration of from $10^{-9}$–$10^{-4}$M).

The reaction is initiated by the addition of tissue and the incubation is for 5 minutes at 30° C. The reaction is terminated by the addition of 4 ml of 7.5% trichloroacetic acid (TCA). 0.2 ml of 0.63% bovine serum albumin is added, the mixture is centrifuged at low speed, and the supernatant is discarded. The precipitate is dissolved in 0.1 ml of 1N NaOH and the TCA precipitation repeated 4 more times. The protein-bound $^{32}$P is then redissolved in NaOH and counted in a scintillation spectrometer. The amount of increase in cpm over control tubes incubated in the absence of cyclic AMP or cyclic AMP analogue represents cyclic-AMP-dependent protein kinase activity. Activity constants are calculated as described previously.

IV. Determination of PDE Inhibitory Activity

In this assay (modified slightly from Filburn and Karn (*Analyt. Biochem.* 52: 505–516 (1973)), the rate of hydrolysis of labeled cyclic AMP to 5'-AMP by PDE is measured by converting the breakdown product (5'-AMP) to adenosine, which can be separated and measured by alumina chromatography. Specifically, tissue from either the firefly lantern or pest is homogenized (10–20 mg/ml) in 6 mM Tris-maleate buffer, pH 7.4. The hydrolysis reaction is run in test tubes containing (in 100 microliters): 80 mM Tris maleate, pH 7.4; 6 mM $MgSO_4$; 10 pmoles tritiated cyclic AMP ($2\times 10^4$ to $2\times 10^5$ cpm, depending upon the activity of the enzyme); 20 microliters of tissue homogenate; and various concentrations of the compound to be tested. In those cases in which the compound is insoluble in aqueous solution at pH 7.4, pH can be varied between pH 6.5 and 9.0 for optimization of solubility. In addition, the test compound can be initially solubilized in either 100% methanol or DMSO and diluted to a final concentration of 10% methanol or DMSO in the assay (in which case solvent controls are run in parallel).

The reaction is started by the addition of homogenate, run for 4 min at 37° C., and terminated by boiling for 90 sec. The 5'AMP formed is then converted to adenosine by the addition of 20 microliters of an aqueous solution of 0.5 Units/ml of 5'-nucleotidase (Sigma, Grade IV), vortexed, and incubated for 30 minutes at 37° C. The second reaction is stopped by addition of 0.4 ml of 0.1N ammonium acetate, pH 4.0. The entire sample is then applied to a $0.5\times 8$ cm column containing neutral alumina prewashed with 20 ml of 0.1N ammonium acetate, pH 4.0. The void volume is discarded and the column is then eluted with 2 ml of 0.1N ammonium acetate, pH 4.0, the eluent collected and counted by liquid scintillation spectrometry. Activity is cpms above that due to a blank which was initially incubated for 0 seconds in the first reaction.

IN VIVO METHODS

To test the effects of PDE inhibition on the pesticidal and pestistatic effects of some of the disclosed compounds, the effects on the feeding behavior of tobacco hornworms (*Manducca sexta*) were investigated. This species is one of the several types of insects particularly susceptible to octopamine type insecticides. The ease of rearing this species from eggs in the laboratory and the ability to maintain them on artificial media, makes it possible to test compounds on large numbers of larvae of the same age.

For testing, single tomato leaves were placed in a closed container, with stems hydrated by means of a small, 3 ml waterfilled bottle. Compounds, dissolved in water or methanol, were sprayed on the tomato leaves with an ultra fine atomizer. Six, 3-day-old larvae were placed on each leaf, allowed to feed for 24–108 hours, and then the percentage of leaf remaining was determined by planimetry, weight, or "blind" visual observation. An active compound or an active synergist was one which resulted in an increase in percentage of leaf remaining, compared with control.

In some cases, test agents were tested for ovacidal activity by dipping groups of 10–50 Manducca eggs in drug solutions for 60 seconds and then determining the percentage of eggs which produced viable larvae. A compound or synergist with active ovacidal activity was one which decreased the percentage of eggs hatched, relative to control.

EXAMPLE 1

Phenylethylamines as Octopamine Agonists

Table 1 shows the structure/activity relationships of phenylethylamines interacting with octopamine sensitive adenylate cyclase of the firefly (*Photinus pyralis*).

TABLE 1

Structure-activity Relationships of Phenylethylamines Interacting with Octopamine-sensitive Adenylate Cyclase

| Compound | (positions 2-6) | β (OH) | α | N | Vmax (% OCT) | $K_a$OCT / $K_a$drug |
|---|---|---|---|---|---|---|
| β-phenylethylamine | — | H | H | $H_2$ | 13 ± 2 | 0.03 |
| (+)-amphetamine | — | H | $CH_3$ | $H_2$ | N.A. | — |
| (±)-phenylethanolamine (-hydroxyphenyl ethylamine) | — | OH | H | $H_2$ | 45 ± 1 | 0.11 |
| (±)-norephedrine (phenylpropanolamine) | — | OH | $CH_3$ | $H_2$ | 8 ± 1 | <0.09 |
| (±)-o-octopamine | 2-OH | OH | H | $H_2$ | 23 ± 1 | 0.05 |
| (±)-m-octopamine (norphenylephrine) | 3-OH | OH | H | $H_2$ | 9 ± 1 | 0.1 |
| (−)-phenylephrine | 3-OH | OH | H | $HCH_3$ | 17 ± 1 | <0.2 |
| tyramine | 4-OH | H | H | $H_2$ | 57 ± 1 | 0.15 |
| (±)-p-hydroxyamphetamine | 4-OH | H | $CH_3$ | $H_2$ | 8 ± 3 | <0.05 |
| (±)-p-octopamine | 4-OH | OH | H | $H_2$ | 81 ± 1 | 0.06 |
| (±)-p-octopamine | 4-OH | OH | H | $H_2$ | 100 ± 1 | 1.0 |
| (−)-p-octopamine | 4-OH | OH | H | $H_2$ | 101 ± 2 | 1.3 |
| (±)-N—methyloctopamine (synephrine) | 4-OH | OH | H | $HCH_3$ | 108 ± 10 | 1.8 |
| (±)-α-methyloctopamine (p-hydroxynorephedrine) | 4-OH | OH | $CH_3$ | $H_2$ | 44 ± 2 | 0.05 |
| (±)-N,N—dimethyl-octopamine | 4-OH | OH | H | $(CH_3)_2$ | 43 ± 4 | 0.9 |
| (±)-α-methylsynephrine (p-hydroxyephedrine) | 4-OH | OH | $CH_3$ | $HCH_3$ | 7 ± 2 | <0.01 |
| p-hydroxymandelic acid | 4-OH | OH | $OHO^F$ | — | N.A.* | — |
| isoxsuprine | 4-OH | OH | $CH_3$ | 1** | N.A. | — |
| p-methoxphenylethylamine (p-methoxytyramine) | 4-$OCH_3$ | H | H | $H_2$ | 6 ± 3 | 0.10 |
| p-fluoro-phenyl-ethanolamine | 4-F | OH | $H_2$ | $H_2$ | 72 ± 8 | 0.11 |
| 2,4-dichlorophenyl-ethanolamine | 2-Cl,4-Cl | OH | H | $H_2$ | 14 ± 1 | 0.67 |
| m-chloro-octopamine | 3-Cl,4-OH | OH | H | $H_2$ | 77 ± 1 | 0.28 |
| dopamine | 3-OH,4-OH | H | H | $H_2$ | 4 ± 1 | 0.26 |
| N—methyldopamine | 3-OH,4-OH | H | H | $HCH_3$ | 11 ± 1 | 0.19 |
| (−)-nonrepinephrine | 3-OH,4-OH | OH | H | $H_2$ | 72 ± 1 | 0.13 |
| (−)-epinephrine | 3-OH,4-OH | OH | H | $HCH_3$ | 75 ± 2 | 0.20 |
| (−)-isoproterenol | 3-OH,4-OH | OH | H | $HCH(CH_3)_2$ | 19 ± 1 | <0.03 |
| (±)-normetanephrine | 3-$OCH_3$,4-OH | OH | H | $H_2$ | 68 ± 2 | 0.07 |
| salbutamol | 3-$CH_2$—OH,4-OH | OH | H | $HC(CH_3)_3$ | N.A. | — |
| zinterol | 3-$NHSO_2CH_3$,4-OH | OH | H | 2** | N.A. | — |

*No Activity

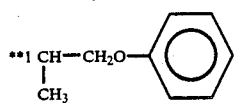

**1

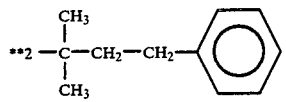

**2

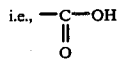

i.e., —C—OH
       ‖
       O

It can be seen that in most instances the half-maximal activation constant $K_a$ for the desired pest controlling compound ranges between less than 0.01 of (±)-p-octopamine to greater than (±)-p-octopamine, whereas the Vmax ranges from less than 4 to 108% of Vmax of octopamine. Examples of compounds satisfying the criteria of most preferred octopamine agonists ($K_a^{oct}/K_a^B > 0.1$; Vmax > 10%) are p-octopamine, N-methyloctopamine, p-fluoro- phenylethanolamine, and 2,4-dichlorophenylethanolamine. As will be shown later, the pesticidal activity of all four of these examples is synergized by combination with a compound having phosphodiesterase inhibitory activity. Note here that m-octopamine has much less activity than the active positional isomer, p-octopamine. As will be shown below, and confirming the in vitro/in vivo correlation, m-octopamine also has much less pesticidal activity than p-octopamine, and the activity shows much less synergism.

EXAMPLE 2

Clonidines as Octopamine Agonists

A number of clonidine analogues were investigated as octopamine agonists in the octopamine receptor of the firefly lantern. Inhibitory properties were also tested. Table 2 shows the results of these experiments.

TABLE 2
OCTOPAMINE RECEPTOR ACTIVITY OF THE CLONIDINES

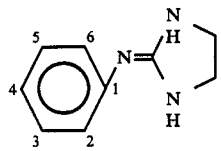

| | | Vmax (% OCT) | $\frac{K_aOCT}{K_adrug}$ | $(\mu m)^{Ki}$ |
|---|---|---|---|---|
| NC 10 | — | N.A. | N.A. | 190 |
| NC 12 | 4-Br | 34 | 3.0 | — |
| NC 8 | 2-Cl, 4-Cl | 47 | 3.7 | — |
| NC 7 | 2-CH$_3$, 4-Cl | 68 | 9.8 | — |
| NC 9 | 2-CH$_3$, 4-CH$_3$ | 78 | 5.1 | — |
| NC 2 | 2-Cl, 5-Cl | 9 | 1.1 | 23 |
| NC 6 | 2-Br, 6-Br | 35 | 2.1 | — |
| clonidine | 2-Cl, 6-Cl | 35 | 0.95 | 20 |
| NC 4 | 2-CH$_3$, 6-CH$_3$ | 80 | 0.41 | — |
| NC 5 | 2-CH$_2$CH$_3$, 6-CH$_2$CH$_3$ | 97 | 19.0 | — |
| NC 3 | 2-Cl, 4-Cl, 5-Cl | 80 | 2.8 | — |
| NC 11 | 2-Cl, 4-Cl, 6-Cl | 60 | 1.9 | — |
| NC 13 | 2-CH$_3$, 4-CH$_3$, 6-CH$_3$ | 112 | 4.3 | — |
| NC 14 | 2-Cl, 4NH$_2$, 6-Cl | 29 | 0.7 | 440 |
| NC 15 | 2-Cl, 4-N(CH$_3$)$_2$, 6-Cl | 38 | 1.9 | — |
| NC 16 | 2-Cl, 4-NCH$_3$(CH$_2$CH$_2$Cl), 6-Cl | 6 | 4.8 | 10 |
| NC 17 | 2-Cl, 4-CH$_2$NCH$_3$(CH$_2$CH$_2$Cl), 6-Cl | N.A. | N.A. | 250 |

Among the findings resulting from this data is the fact that several clonidine derivatives (some having low mammalian potency) are extremely potent octopamine agonists. For example, NC 5 is almost 20 times more potent than octopamine and has an equivalent Vmax. This makes this compound the most potent octopamine agonist yet discovered. Several other compounds are also more potent than octopamine. From the compounds shown in Table 2, two examples (NC5 and NC7) which satisfy the criteria as most preferred octopamine agonists will be shown below to be pesticides, and to have their pesticidal activity markedly synergized by phosphodiesterase inhibition.

EXAMPLE 3

Formamidines as Octopamine Agonists

FIG. 1 shows the agonist activity of three formamidine compounds using the firefly lantern octopamine receptor. This Figure indicates that mono-demethylchlordimeform (DCDM) (Ka ratio=6; V$_{max}$=76%) and di-demethylchlordimeform (DDCDM) (Ka ratio=4; V$_{max}$=68%) have greater potency than octopamine. Of interest, as will be shown later, is the fact that the relative potency of mono demethylchlordimeform (DCDM) and didemethylchlordimeform (DDCDM) as per octopamine agonist activity parallel their pesticidal activity in vivo. Thus, against the octopamine receptor, DCDM is 50% more potent than DDCDM; similarly, as will be shown below, DCDM is more potent in inhibiting feeding behavior of tobacco hornworms. Also shown in FIG. 1 is the fact that chlordimeform (CDM), which is converted in insects to DCDM, has a Ka ratio of 0.5 and a V$_{max}$ of about 10%. As will be shown later, PDE inhibition markedly increases the pesticidal activity of all three formamidines.

Figure 2:
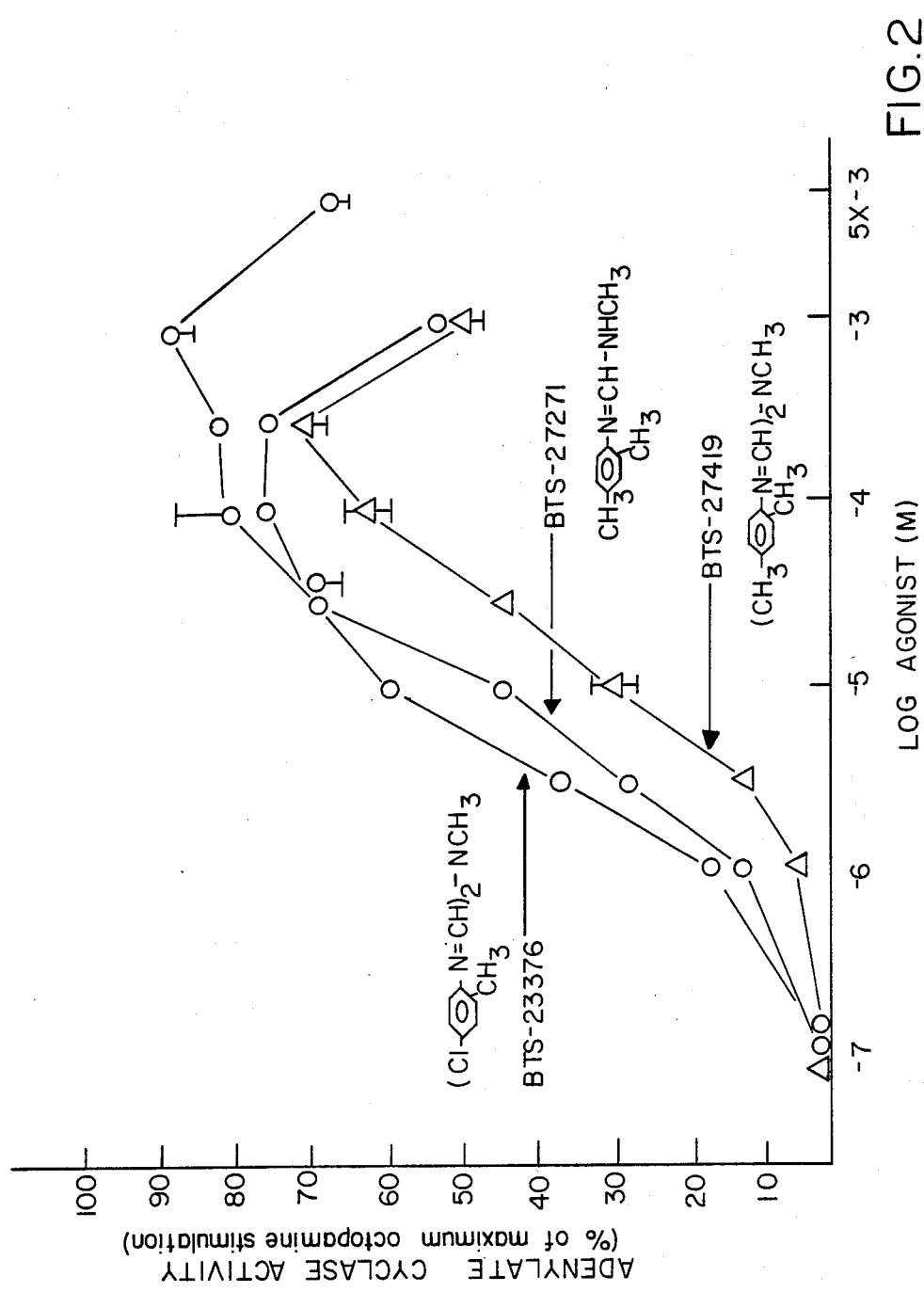
FIG. 2 shows the effect of three formamidines on octopamine activated adenylate cyclase in the firefly light organ.

FIG. 2 shows the effect of three other formamidines on octopamine-activated adenylate cyclase.

EXAMPLE 4

Figure 3:
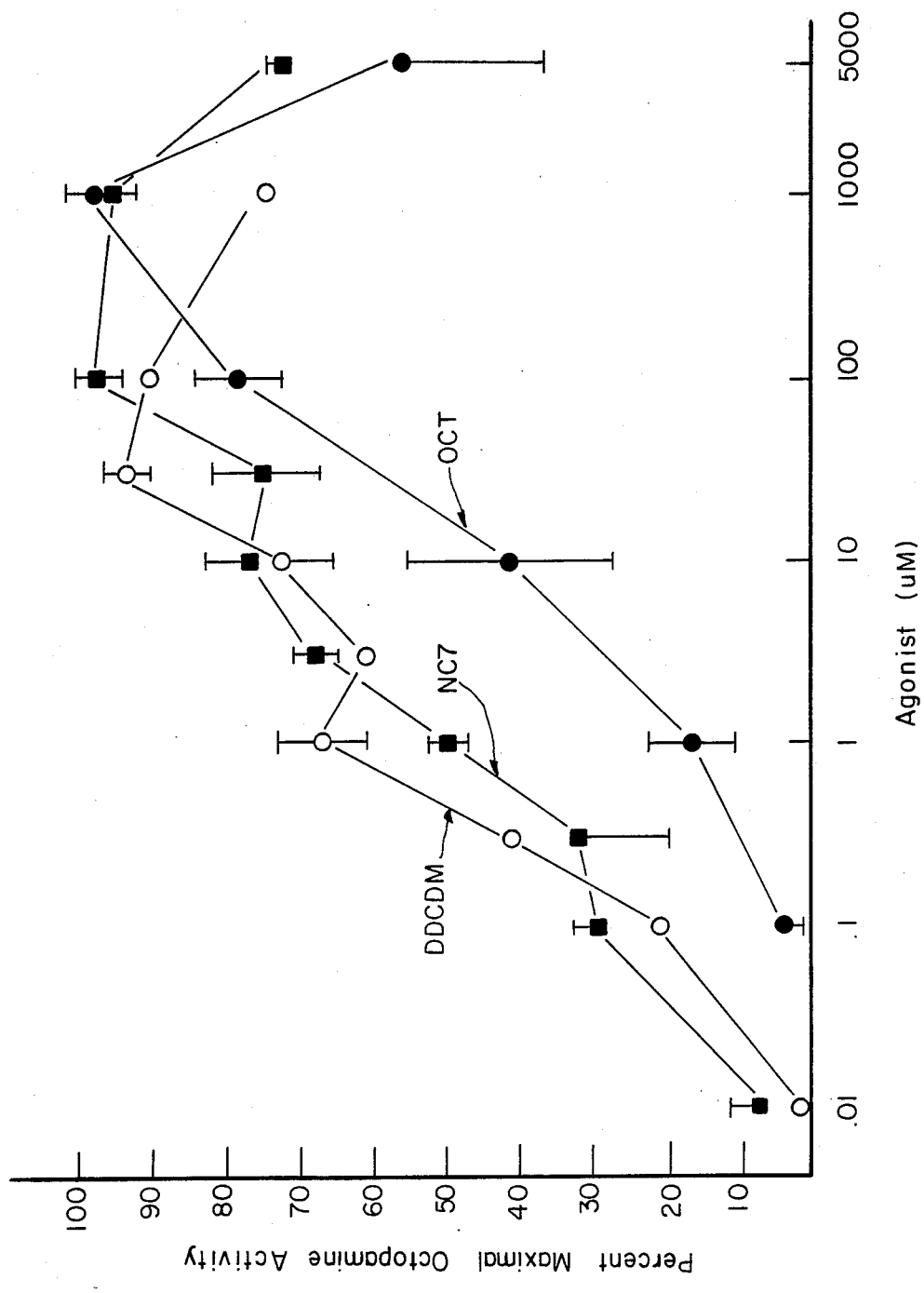
FIG. 3 shows that three compounds, octopamine, NC7 (a clonidine) and DDCDM, are potent activators of adenylate cyclase in the nerve cord of the tobacco hornworm.

Demonstration of Octopamine Agonist Activity Measured in Tissue from an Insect Pest In order to show that adenylate cyclase activation in tissue from an insect pest can also be used to define octopamine agonists, members of three chemical groups (phenylethanolamines, phenyliminoimidazolidines, and formamidines) were tested for their ability to activate adenylate cyclase in broken cell preparations of insect nerve cord. FIG. 3 shows that octopamine, NC7 (see Table 2), and DDCDM were potent activators of adenylate cyclase in nerve cord of tobacco hornworm. All three of these compounds fulfilled the criteria of being most preferred octopamine agonists. As will be described below, all of these compounds have pesticidal activity, and their antifeeding effects are greatly enhanced by PDE inhibition.

EXAMPLE 5

Figure 4:
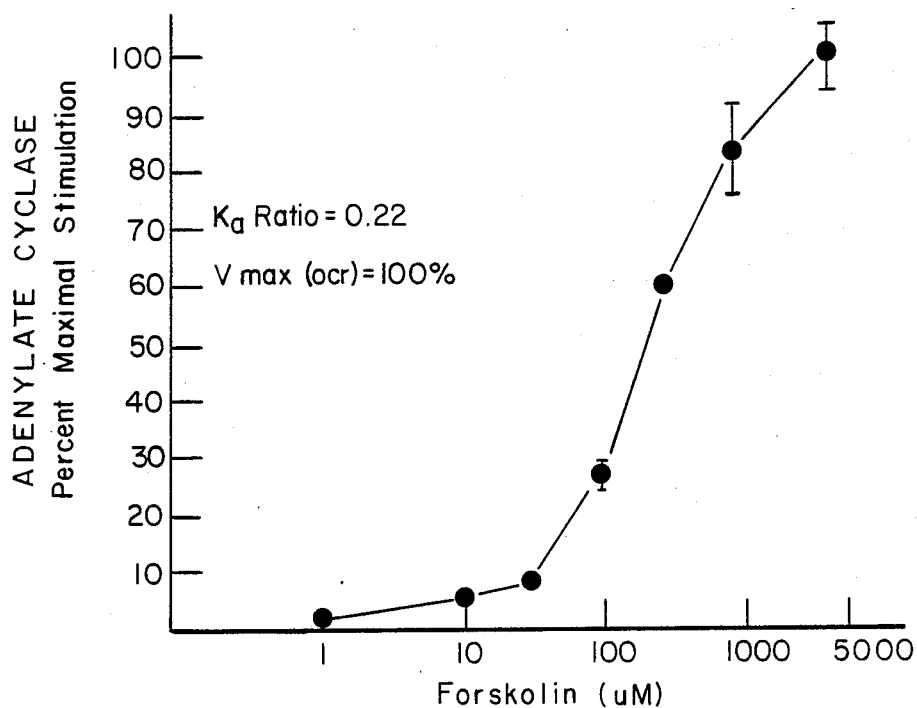
FIG. 4 shows the effect of forskolin in activating adenylate cyclase in firefly lantern. $K_a$ ratio=0.22; $V_{max}$=100%.
Figure 5:
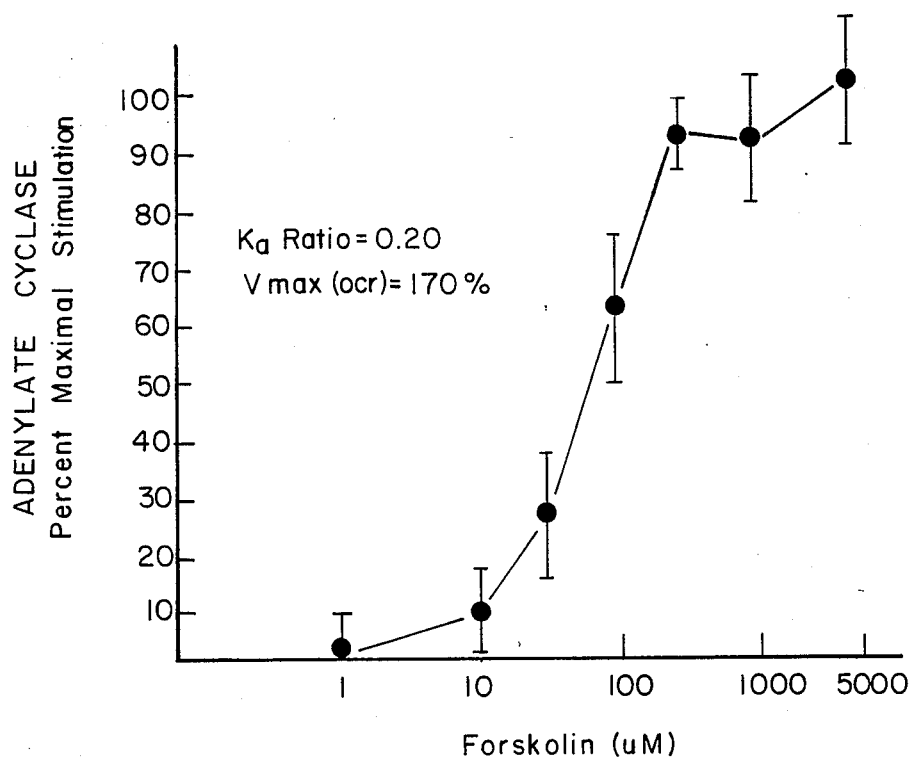
FIG. 5 shows the effect of forskolin in activating adenylate cyclase activity in broken cell preparations from the nerve cord of tobacco hornworm larvae. $K_a$ ratio=0.20; $V_{max}$=about 100%.

A Direct Stimulator of Adenylate Cyclase in the Firefly Lantern and in Pest Tissue FIG. 4 shows the effect of forskolin in directly activating adenylate cyclase in firefly lantern. FIG. 5 also shows the effect of forskolin in directly activating adenylate cyclase activity in broken cell perparations from the nerve cord of tobacco hornworm larvae. In both tissues, forskolin fulfills the criteria of a preferred enzyme activator. As will be shown below, forskolin has activity as a pesticide and this activity is synergized by phosphodiesterase inhibition.

EXAMPLE 6

Figure 6:
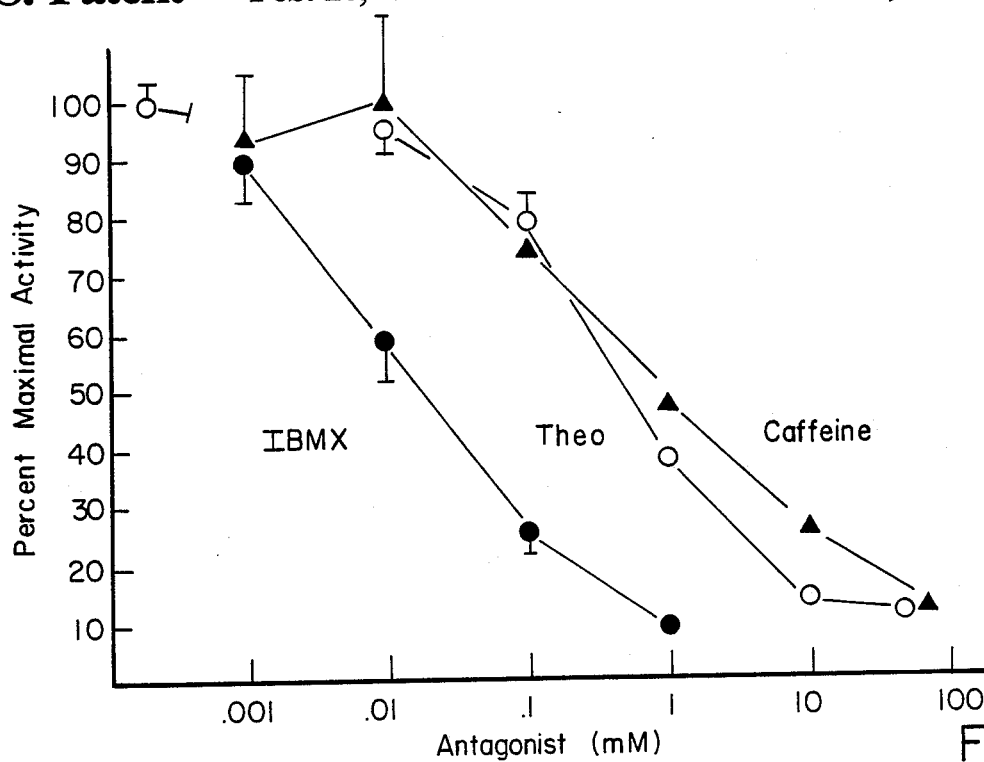
FIG. 6 shows the effect of IBMX, theophylline and caffeine as phosphodiesterase inhibitors against firefly phosphodiesterase enzyme.

Comparison of PDE Inhibitors on the Phosphodiesterase Enzyme from the Firefly Lantern As described above, compounds (A) useful as synergists are those which can inhibit phosphodiesterase enzyme activity with a V$_{max}$-inhibition more than 50% and an IC$_{50}$-inhibition of less than 10 mM, preferably less than 2.5 mM. FIG. 6 shows the effects of three methylxanthines, IBMX, theophylline, and caffeine, active as phosphodiesterase inhibitors against the Firefly phosphodiesterase enzyme. Although all three compounds fulfill the criteria as active synergists, the results show that the $IC_{50}$ for IBMX is less than those for the other two compounds, indicating that IBMX is a more potent inhibitor of the enzyme.

As will be shown below, all three compounds are able to synergize the pesticidal activity of Group B compounds.

Figure 7:
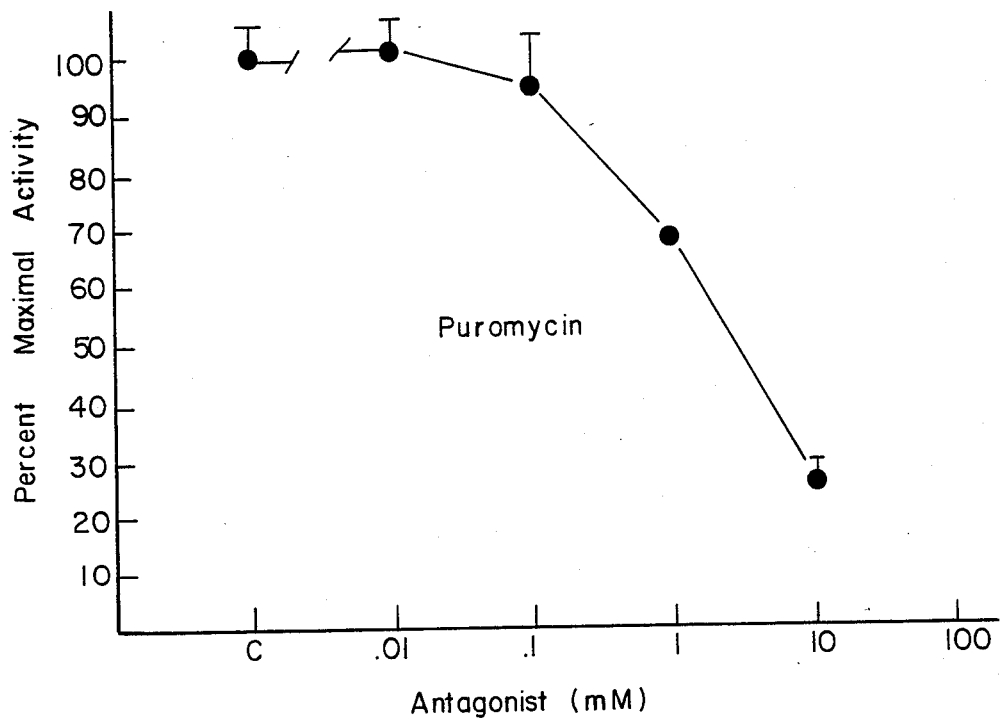
FIG. 7 shows the effect of puromycin inhibition of PDE activity the firefly light organ.

To further demonstrate the generality of the findings as related to PDE inhibition, another compound was defined which was structurally unrelated to the methylxanthines but which was an effective phosphodiesterase inhibitor. FIG. 7 shows that puromycin inhibited PDE activity with an $IC_{50}$-inhibition of less than 2 mM and $V_{max}$ greater than 70%. As will be shown below, puromycin is also able to act as a pesticide synergist.

EXAMPLE 7

Figure 8:
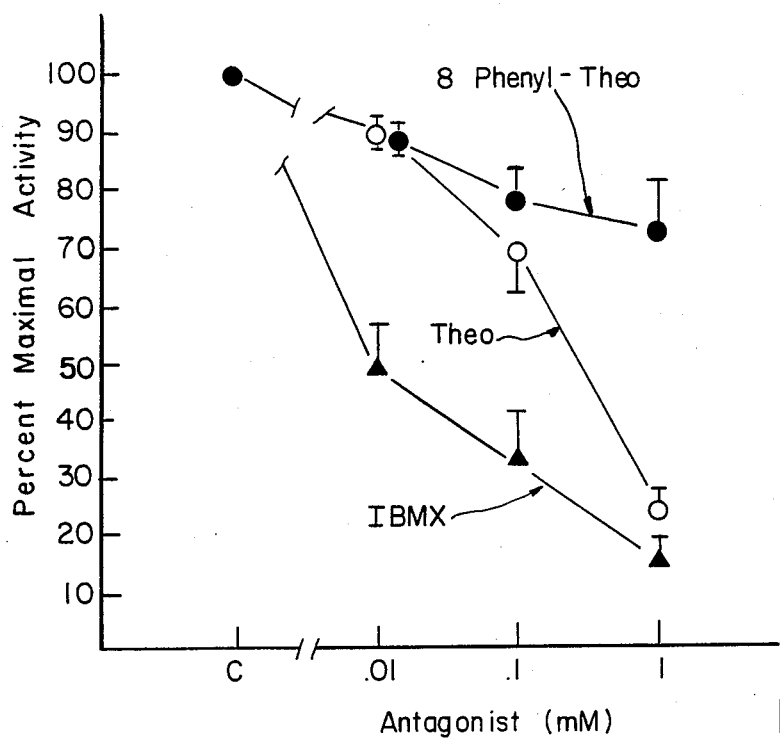
FIG. 8 shows the effect of IBMX, theophylline and 8-phenyltheophylline as inhibitors of the phosphodiestrase enzyme of hornworm nerve cord.

Comparison of PDE Inhibitors on the Phosphodiesterase Enzyme from Insect Pest Tissue To confirm the use of the firefly light organ as a general tissue by which to define useful compounds, other experiments were run using nerve tissue from an insect pest. FIG. 8 shows the effect of IBMX and theophylline on PDE activity in a broken cell preparation from tobacco hornworm larvae. As can be seen, the pattern of inhibition in the hornworm is quite similar to that in the firefly light organ. As will be shown below, when tested against living tobacco hornworm larvae, both IBMX and theophylline were able to synergize the pesticidal activity of Group B compounds.

To further confirm that phosphodiesterase inhibitory activity is the criterion for determining the synergistic potential of a compound, a weakly active methylxanthine analogue was studied. FIG. 8 shows that 8-phenyl-theophylline failed to inhibit phosphodiesterase activity by more than 30%, and therefore fell outside of the criteria defined above for a PDE inhibitor. As will be described below, 8-phenyl-theophylline had very little activity as a pesticide synergist.

EXAMPLE 8

Demonstration of Increased Cyclic AMP Content in Pest Nerve Cord Caused by a Combination of a Phosphodiesterase Inhibitor and an Octopamine Agonist As described earlier and as shown in Scheme I, the pesticidal activity of octopamine agonists is mediated through the increased formation of cyclic AMP within the cells of the insect pest. In order to directly demonstrate that a PDE inhibitor, as defined above, can augment the increase in cyclic AMP caused by an octopamine agonist (as defined above) in an insect pest, further experiments were run using intact nerve cords of tobacco hornworms. These intact nerve cords were incubated under physiological conditions in the presence of octopamine, NC7, or DDCDM, first in the absence of a PDE inhibitor and then in the presence of 0.1 mM IBMX. After 5 minutes, the intact nerve cord was quickly treated to release all cyclic AMP which was present within the tissue.

Table 3 compares the levels of cyclic AMP within nerve tissue under different treatments. As can be seen, with all three octopamine agonists (octopamine, NC7, and DDCDM), addition of IBMX markedly increased the level of cyclic AMP within the nerve tissue.

TABLE 3

| | Effect of PDE Inhibition of Increasing Cyclic AMP in Insect Pest Tissue | |
|---|---|---|
| | Cyclic AMP Content (Fold-increase over Control) | |
| Compound | −IBMX | +0.1 mM IBMX |
| Octopamine | 0.9 ± 0.3 | 6.4 ± 1.0 |
| NC 7 | 2.2 ± 0.2 | 13.9 ± 3.0 |
| DDCDM | 5.4 ± 3.8 | 11.1 ± 2.7 |

Also of considerable interest was the fact that, consistent with the invention, the level of cyclic AMP within the tissue paralleled pesticidal activity. For example, in the absence of the synergist, octopamine caused little elevation of cyclic AMP, and likewise had little pesticidal activity (see FIGS. 9, 10 below). In the presence of IBMX, however, octopamine considerably elevated both cyclic AMP content and pesticidal activity.

EXAMPLE 9

In Vivo Tests of Compositions Containing A PDE Inhibitor and Octopamines

Figure 9:
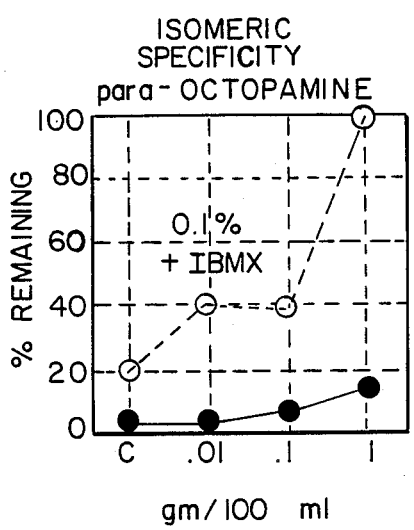
FIG. 9 shows an in vivo test of leaf-eating activity in the presence of p-octopamine alone or p-octopamine plus 0.1% IBMX.

This and the following series of examples demonstrate, in vivo, the effects of PDE inhibitors on increasing pesticidal (pestistatic) or ovacidal activity of compounds of Type B (see Scheme I). FIG. 9 shows the percent leaf remaining at 72 hours following spraying of a series of matched tomato leaves with various concentrations of (±)-p-octopamine or (±)-p-octopamine in the presence of 0.1% IBMX. Comparison of the results shows that the addition of IBMX to (±)-p-octopamine greatly increases the percent leaf remaining, thus acting as a synergist.

Figure 10:
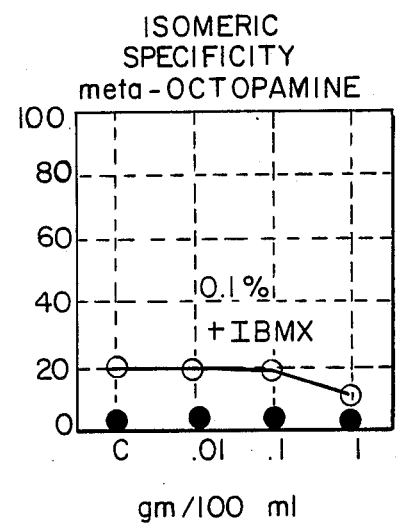
FIG. 10 shows the in vivo test of leaf-eating activity in the presence of m-octopamine alone or m-octopamine plus 0.1% IBMX.

Of interest, and further confirming the invention are the results shown in FIG. 10. Here (±)-m-octopamine, an octopamine analogue which falls short of the in vitro criteria of a most preferred octopamine agonist, was tested in the absence and presence of IBMX. Although IBMX had a very small inhibitory effect by itself, combination with m-octopamine failed to increase pesticidal activity.

EXAMPLE 10

In Vivo Tests of Compositions Containing a PDE Inhibitor and Formamidines

A. Leaf Test

Table 4 below shows the results obtained upon testing tomato leaves in the presence of CDM, DCDM, and DDCDM, with or without the phosphodiesterase inhibitor IBMX. The data indicates clearly that addition of IBMX at 0.1 g/100 ml to the mixture markedly synergized the ability of each of the formamidines to inhibit consumption of the leaf.

Figure 11:
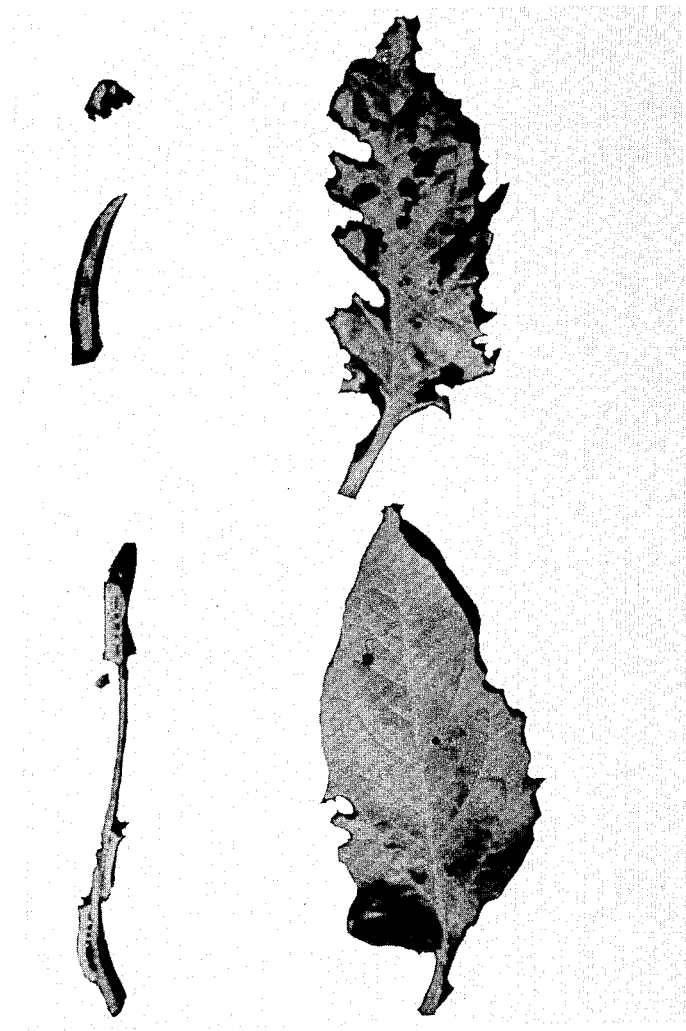
FIG. 11 shows four tobacco leaves 72 hours after treatment with vehicle alone, 0.1% DDCDM; 0.1% IBMX; or a combination of 0.1% DDCDM and 0.1% IBMX.

For clarity of demonstration of this effect, FIG. 11 shows 4 leaves 72 hours after treatment with either vehicle alone (upper left); 0.1% DDCDM (upper right); 0.1% IBMX (lower left); or a combination of 0.1% DDCDM and 0.1% IBMX (lower right). As can be seen, the tobacco hornworms have almost entirely consumed the leaves treated with vehicle or IBMX and have eaten substantial amounts of the leaf treated with DDCDM. The leaf treated with the combination of IBMX and DDCDM, however, is virtually untouched.

TABLE 4

| Agonist (gm/100 ml) | % Leaf Remaining | |
|---|---|---|
| | No PDE Inhibitor | PDE Inhibitor (0.1 g/100 ml) |
| CDM   C* | <5 | IBMX  15 |
| $10^{-4}$ | <5 | 50 |
| $10^{-3}$ | <5 | 65 |
| $10^{-2}$ | <5 | 85 |
| $10^{-1}$ | 70 | 90 |
| 1 | 90 | 90 |
| DCDM   C* | <5 | IBMX  20 |
| $10^{-4}$ | <5 | 75 |
| $10^{-3}$ | 45 | 90 |
| $10^{-2}$ | 95 | 98 |
| DDCDM   C* | 5 | IBMX  22 |
| $10^{-3}$ | 5 | 20 |
| $10^{-2}$ | 7 | 85 |
| $10^{-1}$ | 30 | 98 |
| 1 | 100 | 100 |

*Control = no Agonist

B. Ovacidal Properties

Table 5 shows the ovacidal properties of DCDM and CDM in the presence and absence of IBMX as a phosphodiesterase inhibitor.

TABLE 5

| Agonist (gm/100 ml) | % Living Larvae | |
|---|---|---|
| | No PDE Inhibitor | PDE Inhibitor (0.1 g/100 ml) |
| DCDM   C* | 80 | IBMX  90 |
| $10^{-2}$ | 50 | 10 |
| $10^{-1}$ | 50 | 3 |
| 1 | 2 | 2 |
| CDM   C* | 80 | IBMX  90 |
| $10^{-2}$ | 60 | 10 |
| $10^{-1}$ | 25 | 10 |
| 1 | 2 | 2 |

*Control = no agonist

The results indicate that the addition of IBMX produced a substantial decrease in % living larvae and, therefore, an increase in ovacidal activity. This was particularly apparent at lower concentrations of the agonist; in other words, the PDE inhibitor shifted the dose-response curve to the left and increased the potency of the agonist as an ovacidal agent.

C. Dose-Dependent Effects of Phosphodiesterase Inhibitors

The synergistic effects of PDE inhibitors are apparent at certain, but not all, concentrations of the PDE inhibitor. If the concentration is too low then no substantial synergism occurs. At intermediate concentrations, synergism will occur. At higher concentrations the PDE inhibitor, itself, will inhibit insect feeding. In other words, the PDE inhibitor, at certain concentrations, has pest-controlling activity. This is due to the fact that, even in the absence of an octopamine agonist, the adenyltte cyclase enzyme in the animal slowly produces cyclic AMP which, normally, is easily broken down by the PDE present in the tissue. However, if the PDE is inhibited to a great enough degree, this cyclic AMP will accumulate and act to disrupt the insect's feeding. For example, in the absence of a PDE inhibitor, the cyclic AMP content of hornworm nerve cord incubated for 5 minutes in vitro was found to be 8.9±1.6 pmoles/mg. In the presence of 100 micromoles/liter of IBMX, cyclic AMP content increased to 21.4±0.8 pmoles/mg.

Figure 12:
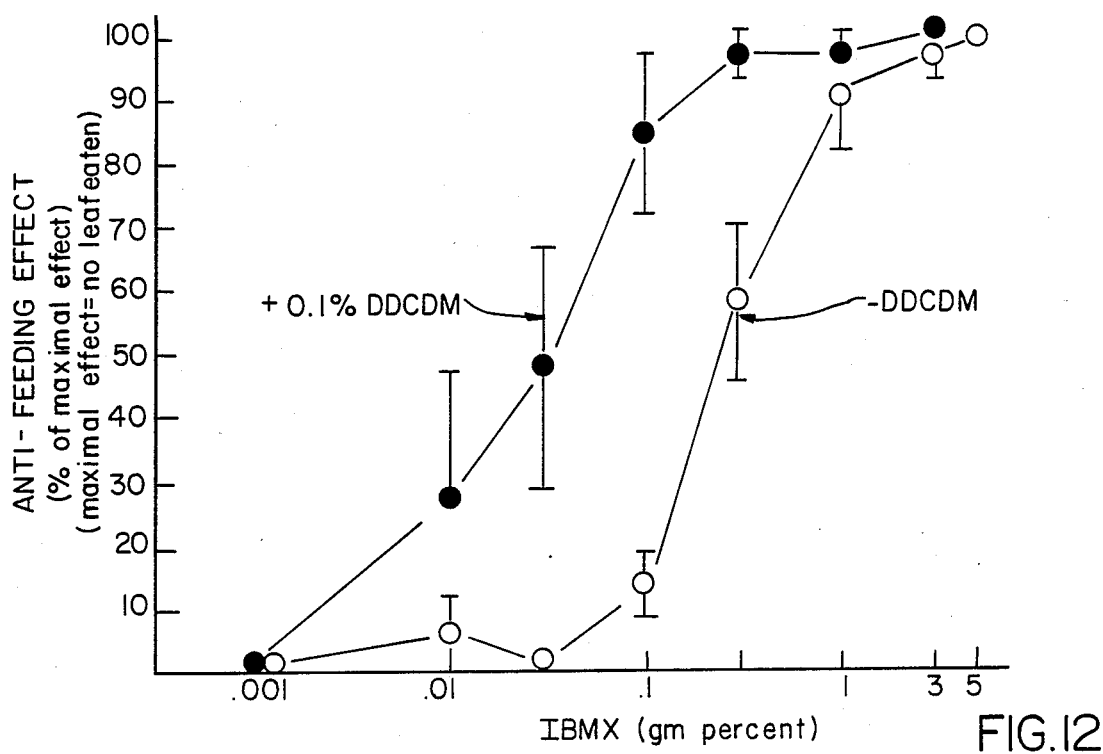
FIG. 12 shows the dose-dependent effect of IBMX on hornworm feeding in the absence or presence of fixed concentrations of DDCDM.

FIG. 12 shows the dose-dependent effect of IBMX on hornworm feeding in the absence or presence of a fixed concentration (0.1%) of DDCDM. As can be seen, at low concentrations (less than 0.001 gm/100 ml) IBMX had no effect by itself and did not increase the activity of DDCDM. At intermediate concentrations (0.01 to 0.3 gm/100 ml), IBMX acted as a synergist of DDCDM. At concentrations of 0.4-5 gm/b 100 ml, IBMX itself acted to inhibit feeding; i.e., it had the properties of a primary pesticide.

Figure 13:
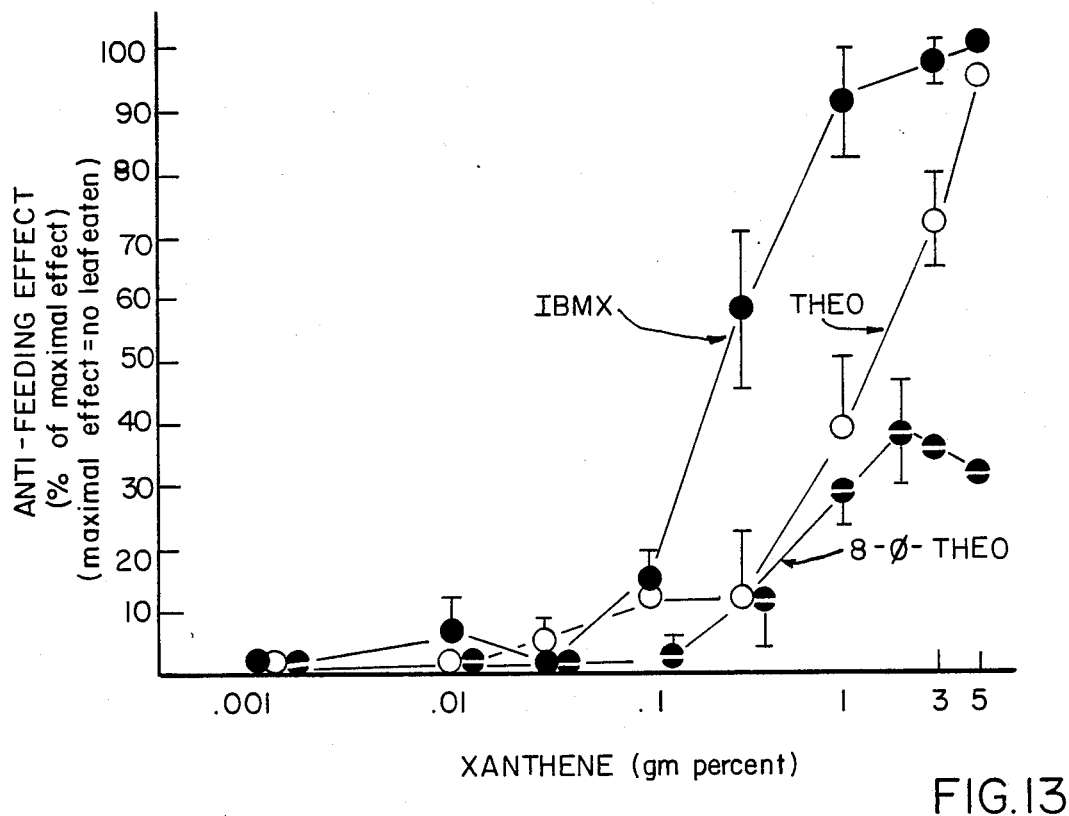
FIG. 13 shows the relationship for three compounds, IBMX, theophylline and 8-phenyl-theophylline between dose sprayed on tomato leaves and the ability to inhibit feeding of tobacco hornworm larvae.

Further data demonstrating that PDE inhibition is the essential property of a compound predicating antifeeding activity is shown in FIG. 13. This graph shows the relationship, for three compounds, between the dose sprayed on tomato leaves and the ability to inhibit feeding of tobacco hornworm larvae. As can be seen, IBMX is more potent than theophylline, and 8-phenyl-theophylline shows the least activity, being unable to inhibit feeding more than 35%, even at a high dose. The relationship between the antifeeding activities of these three compounds is remarkably similar to their relative PDE inhibitory abilities shown in FIG. 8.

The optimal dose of PDE inhibitor as a primary pesticide can be derived from graphs such as FIG. 13. The optimal synergistic concentration of a PDE inhibitor can be derived from graphs such as shown in FIG. 12. In general, optimal synergistic dose will vary, depending upon various factors such as the concentration of primary agonist, the method of application, and the species of pest treated.

D. Other PDE Inhibitors

Figure 14:
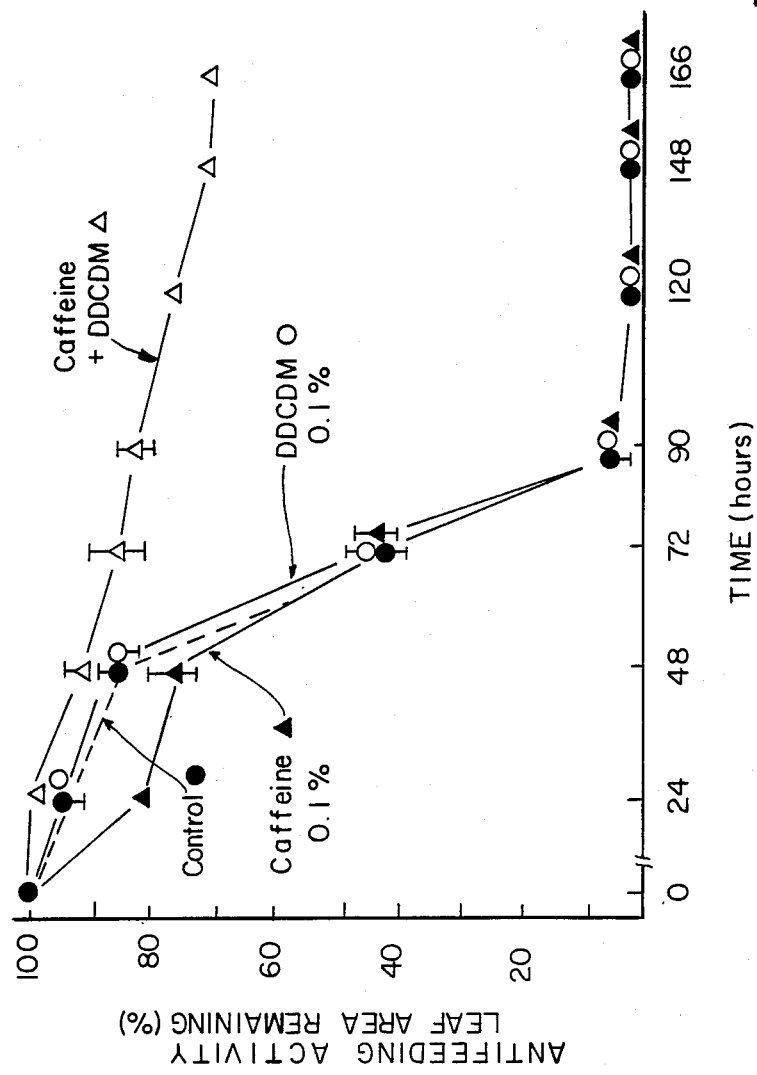
FIG. 14 shows results of a time course experiment noting the progressive eating and diminition of leaf size caused by larvae on leaves treated with caffeine, DDCDM and caffeine plus DDCDM.

The in vivo leaf tests were also carried out for DDCDM alone, caffeine alone, and mixtures of caffeine plus DDCDM. Results are shown in FIG. 14, which depicts results in a different format from dose-response graphs. FIG. 14 is a time-course experiment showing the progressive eating and diminution of leaf size caused by larvae on leaves treated as shown.

The results indicate that mixtures of caffeine with DDCDM are much more powerful in inhibiting leaf feeding than caffeine alone or DDCDM alone. This effect becomes more apparent as time progresses.

Experiments were also carried out with mixtures of theophylline and DDCDM. These results are indicated in Table 6 below:

TABLE 6

| Agonist | % Leaf Remaining (increase over control) |
|---|---|
| Control | 0 |
| DDCDM 0.1 g/100 ml | 0 |
| 1% Theophylline | 11 |
| 1% Theophylline + DDCDM 0.1 gm/100 ml | 61 |

The results indicate that, whereas DDCDM alone or theophylline alone allow only a small amount of leaf to remain (0–11% more than control), the mixture of both allows much more of the leaf to remain.

Figure 15:
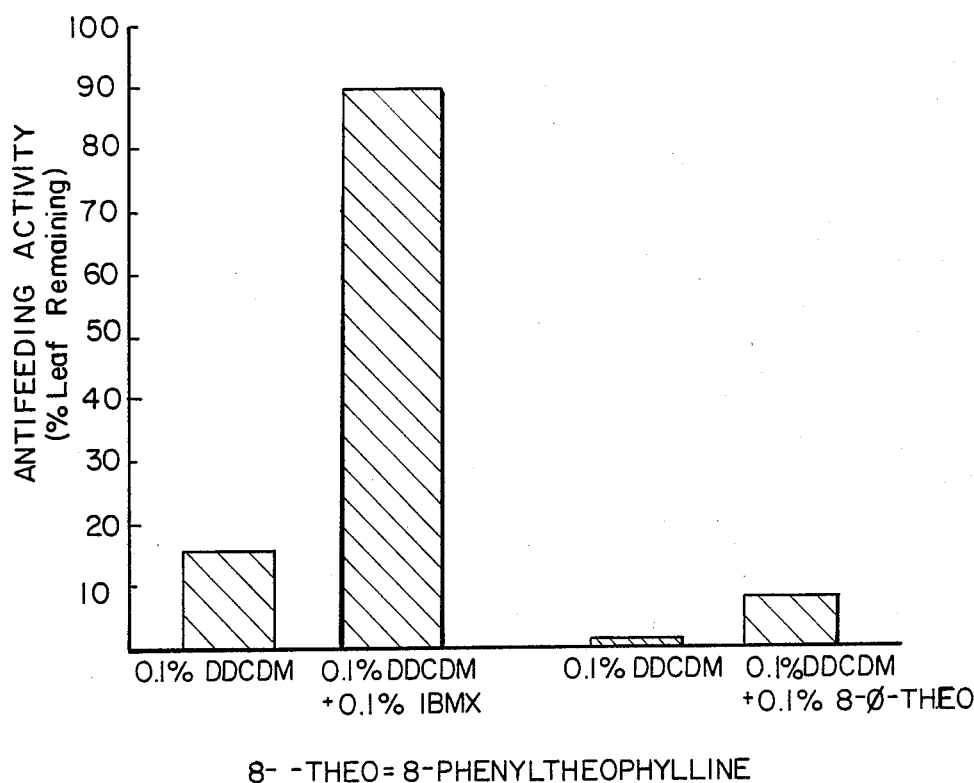
FIG. 15 shows in vivo testing of antifeeding activity of DDCDM compared with either DDCDM plus IBMX or DDCDM plus 8-phenyl-theophylline.

8-Phenyl-theophylline, a compound structurally related to methylxanthine was tested next. FIG. 13 shows that 8-phenyl-theophylline, by itself, had little antifeeding activity. As shown in FIG. 15, results of in vivo testing revealed that, compared with 0.1% IBMX, 0.1% 8-phenyl-theophylline had much less activity as a synergist of 0.1% DDCDM. These results would have been unexpected on the basis of chemical structure alone, but were predicted by the in vitro PDE assay procedure, as shown in FIG. 8, which indicates that 8-phenyl-theophylline has little activity as a PDE inhibitor. These results with 8-phenyl-theophylline further confirm the in vitro/in vivo correlation of the invention.

Figure 16:
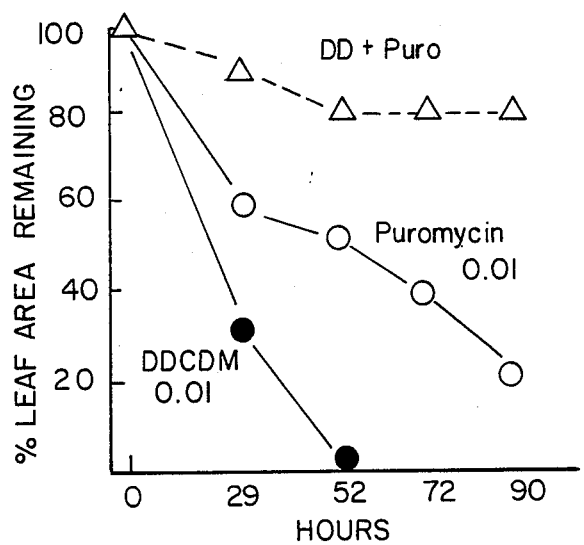
FIG. 16 shows an in vivo test wherein leaves are treated with DDCDM, puromycin or DDCDM plus puromycin.

Experiments were also carried out with the structurally-unrelated PDE inhibitor, puromycin (see FIG. 7), in mixtures with the primary pest compound, DDCDM. These results, which are shown in FIG. 16, demonstrate that puromycin was able to synergize the pesticidal activity of DDCDM. This result further confirms the generality of the findings with PDE inhibition.

EXAMPLE 11

In Vivo Leaf Test of Compositions Containing a PDE Inhibitor and Phenylethanolamines Table 7 shows the results obtained for mixtures comprising various phenylethanolamines in the presence or absence of IBMX as a PDE inhibitor.

TABLE 7

| Agonist (gm/100 ml) | | % Leaf Remaining | |
|---|---|---|---|
| | | No PDE Inhibitor | PDE Inhibitor (0.1 g/100 ml) |
| 4-F—phenylethanol-amine | C* | <5 | IBMX 25 |
| | $10^{-3}$ | <5 | 50 |
| | $10^{-2}$ | <5 | 80 |
| | $10^{-1}$ | <5 | 98 |
| | 0.3 | 25 | 95 |
| 2,4-dichlorophenyl-ethanolamine | C* | <5 | IBMX 20 |
| | $10^{-2}$ | <5 | 30 |
| | $10^{-1}$ | <5 | 50 |
| | 1 | 10 | 80 |
| Synephrine | C* | <5 | IBMX 42 |
| | $10^{-2}$ | <5 | 42 |
| | $10^{-1}$ | <5 | 55 |
| | 1 | 30 | 90 |

*Control = No Agonist

The results show that in all instances, addition of IBMX markedly enhanced the ability of the phenylethanolamines to inhibit the leaf feeding activity of the pest.

EXAMPLE 12

In Vivo Leaf Tests of Compositions Containing a PDE Inhibitor and Phenyliminoimidazolidines (Clonidines).

Mixtures of various clondine derivatives with IMBX were prepared and tested in the aforementioned in vivo tests. Table 8 shows the results.

TABLE 8

| Agonist (gm/100 ml) | | % Leaf Remaining | |
|---|---|---|---|
| | | No PDE Inhibitor | PDE Inhibitor (0.1 g/100 ml) |
| NC 7[1] | C* | 25 | IBMX 30 |
| | $10^{-3}$ | 23 | 48 |
| | $10^{-2}$ | 30 | 85 |
| | $10^{-1}$ | 55 | 95 |
| | $3 \times 10^{-1}$ | 80 | 100 |
| clonidine | C* | 5 | IBMX 35 |
| | $10^{-2}$ | 5 | 55 |
| | $10^{-1}$ | 20 | 55 |
| | 1 | 65 | 63 |
| NC 5[1] | C* | 10 | IBMX 18 |
| | $10^{-3}$ | 10 | 17 |
| | $10^{-2}$ | 15 | 30 |
| | $10^{-1}$ | 30 | 45 |
| | $3 \times 10^{-1}$ | 40 | 70 |
| NC 10[1] | C* | 10 | IBMX 15 |
| | $10^{-3}$ | 5 | 12 |

TABLE 8-continued

| Agonist (gm/100 ml) | % Leaf Remaining | |
|---|---|---|
| | No PDE Inhibitor | PDE Inhibitor (0.1 g/100 ml) |
| $10^{-2}$ | 5 | 15 |
| $10^{-1}$ | 5 | 13 |
| 1 | 5 | 15 |

[1]See Table 2, supra
*Control = No agonist

The data indicate that, with NC7, clonidine, and NC5, addition of IBMX results in substantial increases in the potency of the pest controlling compound. It will be noted that these three pest controlling compounds, on the basis of in vitro testing (Table 2), all satisfied the criteria of being most preferred compounds of type B. Of interest, and further confirming the invention, was the fact that the structural analogue, NC10, was inactive in vivo and was not synergized by the PDE inhibitor. Thus, as can be seen in Table 8, the addition of various concentrations of NC 10 to the PDE inhibitor, IBMX, did not increase antifeeding activity over that of the PDE inhibitor alone. This unexpected result was correctly predicted by the in vitro assay data shown in Table 2, where NC10 had no activity.

EXAMPLE 13

Figure 17:
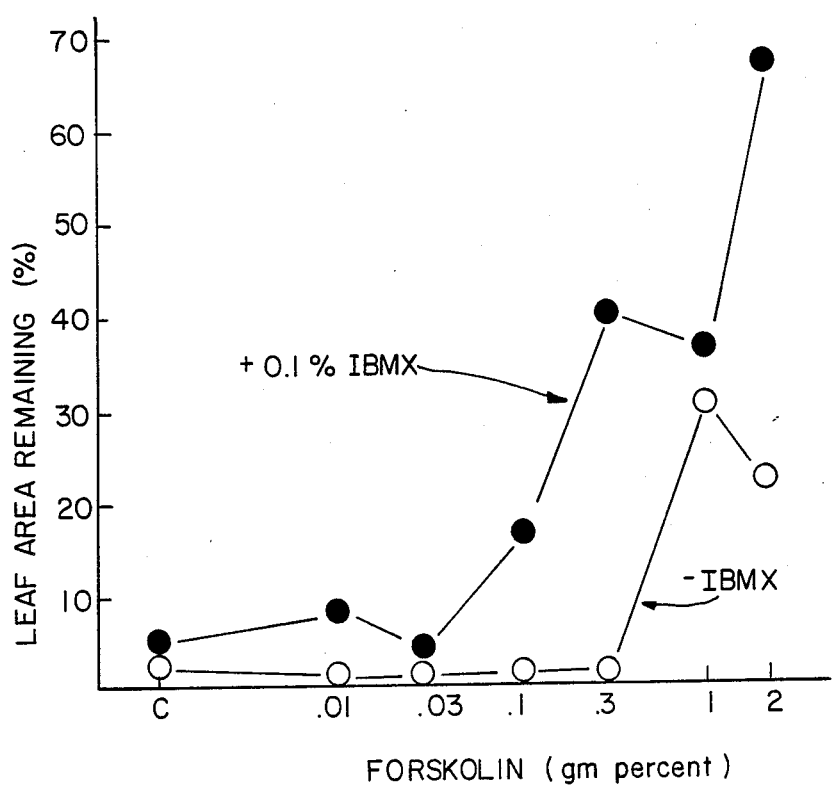
FIG. 17 shows an in vivo leaf test of a composition containing forskolin in the presence or absence of IBMX.

In Vivo Leaf Test of a Composition Containing a PDE Inhibitor and a Direct Enzyme Stimulator As described previously, the diterpene forskolin is an example of a compound which directly stimulates adenylate cyclase, thereby producing cyclic AMP. This example shows that inhibition of PDE enhances the antifeeding activity of forskolin on tobacco hornworm larvae. FIG. 17 shows that forskolin, alone, has antifeeding activity. FIG. 17 also shows that this antifeeding activity is enhanced in the presence of (0.1%) of the PDE inhibitor IBMX.

EXAMPLE 14

Figure 18:
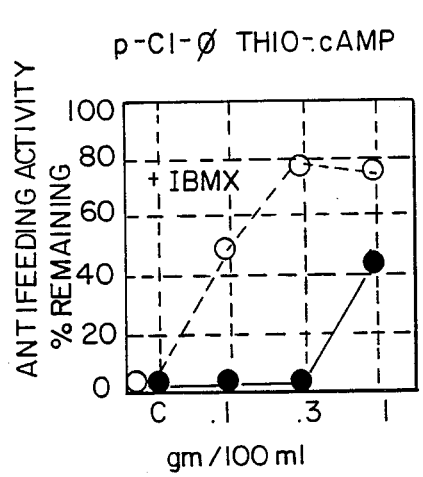
FIG. 18 shows an in vivo antifeeding activity test for the cyclic AMP analogue p-chlorophenylthiocyclic AMP in the presence or absence of IBMX.
Figure 19:
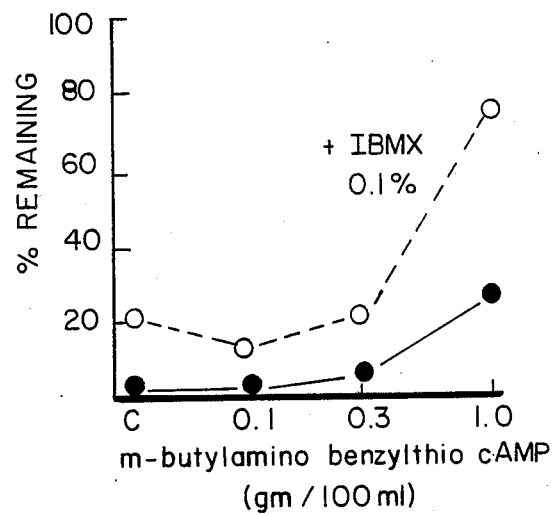
FIG. 19 shows an in vivo antifeeding activity test for leaves treated with n-butylaminobenzylthiocyclic AMP in the presence or absence of IBMX.

In Vivo Leaf Test of a Composition Containing a PDE Inhibitor and a cAMP Analogue Mixtures containing IBMX 0.1% and 2 cyclic AMP analogues were tested by the leaf test. The results are shown in FIG. 18 for p-Cl-phenylthio cyclic AMP, and FIG. 19 for n-butylaminobenzylthio cyclic AMP. As can be seen, both compounds, at a concentration of 1%, also showed some antifeeding activity in the absence of IBMX.

Figure 20:
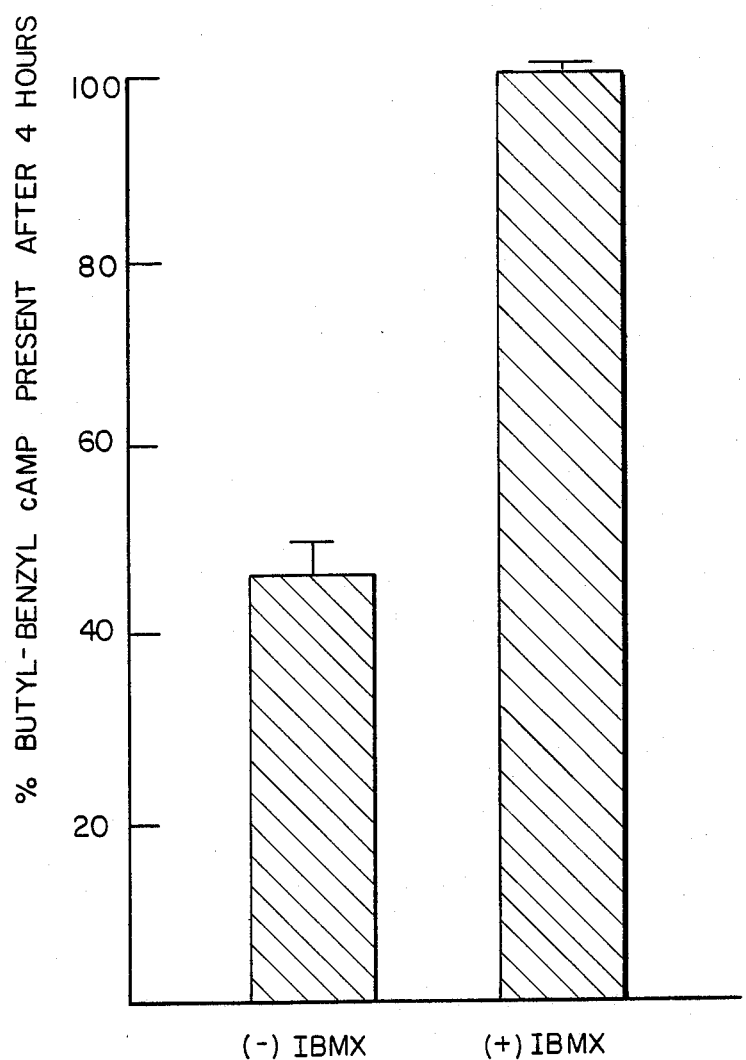
FIG. 20 shows the amount of cyclic AMP analogue butylbenzylthiocyclic AMP remaining in pest tissue in the presence or absence of IBMX.
Figure 21:
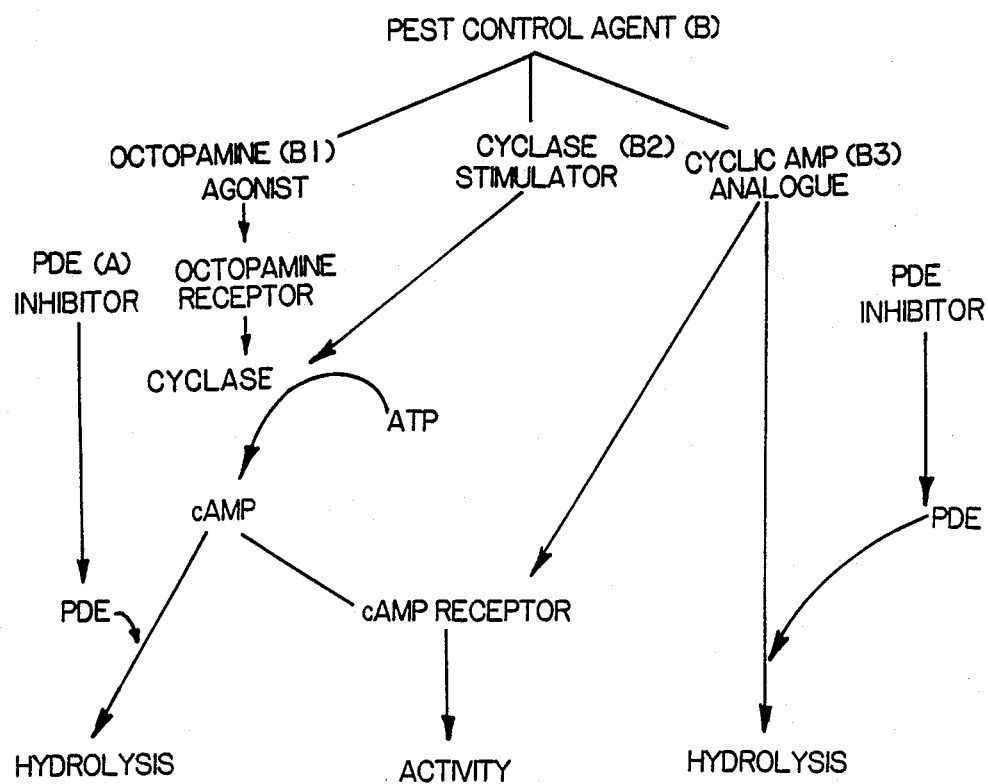
FIG. 21 indicates the three types of pest control agents having pest control activity useful as compounds (B).

It has been previously shown, above, that PDE inhibition can increase the concentration of cyclic AMP in insect tissue. To further confirm the invention this example demonstrates directly that PDE inhibition can also increase the levels of cyclic AMP analogues, such as butyl-benzylthio cyclic AMP, in insect pest tissue. In order to do this, a fixed amount of butyl-benzylthio cyclic AMP was incubated in vitro for 4 hours in the presence of a tissue homogenate from tobacco hornworm nerve cord. In some tubes, IBMX (0.1 mM) was added to inhibit PDE. After the incubation, the amount of butyl-benzylthio cyclic AMP remaining was measured by protein binding assay (Brown et al., supra), using a standard curve based upon butyl-benzylthio cyclic AMP. FIG. 20 shows that addition of IBMX more than doubled the amount of butyl-benzylthio cyclic AMP present after 4 hours.

EXAMPLE 15

Determination of Levels of PDE Inhibitor Compounds in Insects In Vivo

In order to supply further evidence that PDE compounds of type A were exerting their effects through inhibition of PDE, it was determined that these compounds, when applied to the tomato leaves, a) were able to be absorbed by the tobacco hornworms, and b) that the concentration of compound within the insect corresponded approximately to the concentration necessary to cause substantial inhibition of PDE activity in vitro.

To determine this, tobacco hornworms were allowed to feed on tomato leaves treated with a 1% spray of theophylline. This concentration was chosen since it is an amount which, by itself, inhibits feeding in the tobacco hornworm (see FIG. 13). After 72 hours, worms (alive or dead) were removed, quickly rinsed of any compound adhering to their outside cuticle, and then homogenized. The homogenate was centrifuged at $2000 \times g$ for 5 minutes and the supernatant was assayed for theophylline concentration by a standard immuno-enzymatic procedure (Emit-aad ® Theophylline Assay, Syva Company, Palo Alto, Calif.). By this procedure, the internal concentration within the insects was determined to be 4.0 mM. From FIGS. 6, 7 or 8 it will be seen that this concentration of theophylline is sufficient to cause at least 70% inhibition of PDE enzyme activity in vitro. The correspondence between in vitro and in vivo results is remarkably close and serves to further support the invention.

Having now fully described this invention it will be understood by those of skill in the art that the same can be performed within a wide and equivalent range of compositions, parameters, structures, modes of application, pests, formulations, and ranges without effecting the scope of the invention or any embodiment thereof.

What is new and intended to be covered by Letters Patent of the United States is:

1. A pest-controlling composition which comprises:
   (A) a first compound capable of substantially inhibiting a phosphodiesterase enzyme (PDE) of said pest; and
   (B) a second compound having pest-controlling activity towards said pest comprising a substantial octopamine agonist toward an octopamine receptor in said pest;
   wherein said first and second compounds are present in an amount effective to control said pest.

2. The composition of claim 1 wherein said first compound (A) is capable of inhibition of the phosphodiesterase enzyme present in broken cell preparation of the firefly (*Photinus pyralis*) light organ, or in nerve tissue of said pest.

3. The composition of claim 1 wherein the in vitro ratio $Ka^{oct}/Ka^B$ for said compound is greater thatn 0.05; where $Ka^{oct}$ is the agonistic activity constant for ($\pm$)p-octopamine.

4. The composition of claim 3 wherein said ratio is between 0.05 and 1000.

5. The composition of claim 4 wherein said ratio is between 0.1 and 1000.

6. The composition of any of claims 1, 3, 4 or 5 wherein the in vitro % Vmax for said compound, relative to the Vmax for ($\pm$) p-octopamine, is greater than 5%.

7. The composition of claim 6 wherein said % Vmax for is between 10 and upwards of 100%.

8. The composition of claim 1 wherein the in vitro ratio $Ka^{oct}/Ka^B$ for said compound B is greater than 0.1 and the % Vmax for said compound, relative to the Vmax for ($\pm$)-p-octopamine is greater than 10%.

9. The composition of claim 1 wherein said compound (A) has an $IC_{50}$ *inhibition* of less than 10 mM.

10. The composition of claim 9 wherein said $IC_{50}$ inhibition is less than 2.5 mM.

11. The composition of claim 1 in the form of a dust, a powder, a water dispersion, an emulsion or solution.

12. The composition of claim 1 together with a pesticical carrier.

13. A method of controlling a pest which comprises bringing into contact with said pest a pest-controlling amount of the composition of any of claims 1, 2-5, 8 or 9-12.

14. The composition of claim 1 wherein said compound A is isobutylmethylxanthine (IBMX).

15. The composition of claim 1 wherein said compound B is an octopamine agonist, 2-(phenylimino)imidazolidine.

16. A pest controlling composition which comprises:
   (A) isobutylmethylxanthine; and
   (B) 2-(phenylimino)imidazolidine;
   wherein said isobutylmethylxanthine and 2-(phenylimino)imidazolidine are present in an amount effective to control said pest.

* * * * *